United States Patent
Hyohgo et al.

(10) Patent No.: US 9,931,058 B2
(45) Date of Patent: Apr. 3, 2018

(54) EXHALATION MEASUREMENT DEVICE AND CONTROL METHOD THEREFOR

(71) Applicant: Panasonic Healthcare Holdings Co., Ltd., Minato-ku, Tokyo (JP)

(72) Inventors: Jun'ichi Hyohgo, Ehime (JP); Takeshi Ohsora, Ehime (JP); Toru Kawamoto, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 379 days.

(21) Appl. No.: 14/891,964

(22) PCT Filed: May 21, 2014

(86) PCT No.: PCT/JP2014/002676
§ 371 (c)(1),
(2) Date: Nov. 17, 2015

(87) PCT Pub. No.: WO2014/188720
PCT Pub. Date: Nov. 27, 2014

(65) Prior Publication Data
US 2016/0089058 A1 Mar. 31, 2016

(30) Foreign Application Priority Data

May 23, 2013 (JP) .................................. 2013-109122

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/087* (2013.01); *A61B 5/091* (2013.01); *A61B 5/7203* (2013.01);
(Continued)

(58) Field of Classification Search
CPC ....... A61B 5/097; A61B 5/087; A61B 5/7203; A61B 5/091; A61B 2560/0257; A61B 2560/0223; A61B 2562/0247
See application file for complete search history.

(56) References Cited

U.S. PATENT DOCUMENTS

2004/0144178 A1 7/2004 Ohmi et al.
2007/0151321 A1 7/2007 Ohmi et al.
(Continued)

FOREIGN PATENT DOCUMENTS

EP 1637859 A1 3/2006
EP 1661514 A2 5/2006
(Continued)

OTHER PUBLICATIONS

European Search Report from the corresponding European Patent Application No. 14800932.7 dated Jun. 9, 2016.
(Continued)

*Primary Examiner* — Navin Natnithithadha
*Assistant Examiner* — Andrey Shostak
(74) *Attorney, Agent, or Firm* — Shinjyu Global IP

(57) ABSTRACT

Certain implementations relate to an exhalation measurement device that is used in checking pulmonary function, diagnosing asthma, and may perform zero point correction accurately even when there is disturbance. The exhalation measurement device may comprise a flow regulator. The flow regulator comprises a first offset adjuster that puts an exhalation inflow component and an exhalation outflow component in a separated state and performs first offset adjustment of an inflow pressure sensor and an outflow pressure sensor, a voltage difference detector that puts the exhalation inflow component and the exhalation outflow component in a linked state and detects an output voltage difference after the first offset adjustment of the inflow
(Continued)

pressure sensor and the outflow pressure sensor, and a second offset adjuster that uses the output voltage difference to perform second offset adjustment of the inflow pressure sensor.

13 Claims, 12 Drawing Sheets

(51) Int. Cl.
 *A61B 5/091* (2006.01)
 *A61B 5/087* (2006.01)
 *A61B 5/00* (2006.01)
(52) U.S. Cl.
 CPC ............... *A61B 2560/0223* (2013.01); *A61B 2560/0257* (2013.01); *A61B 2562/0247* (2013.01)

(56) References Cited

U.S. PATENT DOCUMENTS

| | | | |
|---|---|---|---|
| 2012/0310104 | A1 | 12/2012 | Van Kesteren et al. |
| 2013/0345588 | A1 | 12/2013 | Miki et al. |
| 2015/0105684 | A1 | 4/2015 | Yano et al. |

FOREIGN PATENT DOCUMENTS

| | | | |
|---|---|---|---|
| JP | 2005-010108 A | | 1/2005 |
| JP | 2005-538819 A | | 12/2005 |
| WO | 2004/023997 A1 | | 3/2004 |
| WO | 2011/101776 A1 | | 8/2011 |
| WO | 2012/127794 A1 | | 9/2012 |
| WO | 2013/161286 A1 | | 10/2013 |

OTHER PUBLICATIONS

Search Report from the corresponding International Patent Application No. PCT/JP2014/002676 dated Aug. 19, 2014.

EXHALATION MEASUREMENT DEVICE AND CONTROL METHOD THEREFOR

PRIORITY

This is a National Stage application under 35 U.S.C. § 365 of International Application PCT/JP2014/002676, with an international filing date of May 21, 2014, which claims priority to Japanese Patent Application No. 2013-109122 filed on May 23, 2013. The entire disclosures of International Application PCT/JP2014/002676 and Japanese Patent Application No. 2013-109122 are hereby incorporated herein by reference.

TECHNICAL FIELD

Certain implementations relate to an exhalation measurement device used in checking pulmonary function, diagnosing asthma, and so forth, and to a method for controlling this device.

BACKGROUND

A conventional exhalation measurement device of this type is generally equipped with a flow regulator to obtain the exhalation flow that has been indicated for measuring nitrogen monoxide in exhalation. The function of this flow regulator is to accurately control the exhalation flow by automatically adjusting the flow of exhalation blown in through the inlet of the exhalation measurement device, or by adjusting the flow to a preset level.

This flow regulator also comprises a pressure sensor for controlling the flow very accurately. If the output of this pressure sensor changes over time, technology can be employed, for example, to perform zero point correction of the pressure sensor automatically as soon as the change in output goes over a specific set value, and prevent the occurrence of error in the measurement of pressure and flow.

SUMMARY

With the above flow regulator, if technology is employed, the flow can be adjusted by a pressure sensor that monitors the exhalation pressure and is disposed at the inlet or outlet of the device. Furthermore, if changes over time caused by aging of the pressure sensor or the like cause the output of the pressure sensor to exceed the correctable range, zero point correction of the pressure sensor can be performed with respect to a preset value.

However, when the above-mentioned zero point correction of the pressure sensor is performed, if the user moves the inlet side of the exhalation measurement device, or puts the inlet part in his mouth, gas will flow from the inlet into the interior of the exhalation measurement device, or gas will flow through the inlet to the outside of the exhalation measurement device, so disturbance occurs and zero point correction cannot be performed accurately.

An exhalation measurement device with which perform zero point correction can be performed accurately even when there is disturbance, as well as a method for controlling this device.

To achieve this object, an implementation may comprise a handle component, a flow regulator, a chamber, an opening component, a measurement component, and a pump. The user exhales into the handle component. The flow regulator is provided downstream from the handle component and adjusts the flow of exhalation blown in from the handle component. The chamber is provided downstream from the flow regulator and temporarily stores exhalation. The opening component is provided near the chamber and opens up the flow regulator to atmospheric pressure. In terms of being near the chamber, the opening component may or may not actually contact the chamber. The opening component may be connected to the chamber. The measurement component measures a specific component in exhalation. The pump is provided downstream from the chamber and sends exhalation into the measurement component. The flow regulator has an exhalation inflow component, an exhalation outflow component, a flow adjuster, a driver, an inflow pressure sensor, an outflow pressure sensor, a first offset adjuster, a voltage difference detector, and a second offset adjuster. The exhalation inflow component is where exhalation flows in from the handle component side. The exhalation outflow component is where exhalation flows out to the chamber side. The flow adjuster is provided between the exhalation inflow component and the exhalation outflow component and adjusts the flow of exhalation. The driver moves the flow adjuster. The inflow pressure sensor senses the pressure of the exhalation inflow component. The outflow pressure sensor senses the pressure of the exhalation inflow component. The first offset adjuster causes the driver to move the flow adjuster and create a separated state between the exhalation inflow component and the exhalation outflow component, and performs first offset adjustment of the inflow pressure sensor and the outflow pressure sensor. The voltage difference detector causes the driver to move the flow adjuster and create a linked state between the exhalation inflow component and the exhalation outflow component, and detects the output voltage difference after the first offset adjustment of the inflow pressure sensor and the outflow pressure sensor. The second offset adjuster uses the output voltage difference to perform second offset adjustment of the inflow pressure sensor.

Specifically, the flow regulator may have an exhalation inflow component, an exhalation outflow component, a flow adjuster, a driver, an inflow pressure sensor, an outflow pressure sensor, a first offset adjuster, a voltage difference detector, and a second offset adjuster. The exhalation inflow component is where exhalation flows in from the handle component side. The exhalation outflow component is where exhalation flows out to the chamber side. The flow adjuster is provided between the exhalation inflow component and the exhalation outflow component and adjusts the flow of exhalation. The driver moves the flow adjuster. The inflow pressure sensor senses the pressure of the exhalation inflow component. The outflow pressure sensor senses the pressure of the exhalation inflow component. The first offset adjuster causes the driver to move the flow adjuster and create a separated state between the exhalation inflow component and the exhalation outflow component, and performs first offset adjustment of the inflow pressure sensor and the outflow pressure sensor. The voltage difference detector causes the driver to move the flow adjuster and create a linked state between the exhalation inflow component and the exhalation outflow component, and detects the output voltage difference after the first offset adjustment of the inflow pressure sensor and the outflow pressure sensor. The second offset adjuster uses the output voltage difference to perform second offset adjustment of the inflow pressure sensor.

Thus, in the second offset adjustment, since the exhalation inflow component and the exhalation outflow component are linked, the pressure is the same in the exhalation inflow component and the exhalation outflow component. Accordingly, second offset adjustment of the inflow pressure sensor can be performed on the basis of the value from the outflow pressure sensor that has undergone proper zero point correction by the first offset adjustment.

Therefore, even if gas should flow in from the handle component side to the exhalation inflow component, or if gas should flow out from the exhalation inflow component side to the handle component side, it will still be possible to perform the proper zero point correction on the inflow pressure sensor.

Also, this allows the offsetting of the inflow pressure sensor and the outflow pressure sensor to be performed according to the measurement environment.

Therefore, even if there are changes over time, zero point correction of the inflow pressure sensor and the outflow pressure sensor will always be possible under an atmospheric pressure environment during measurement, so the measurement will not be affected by changes over time, and measurement can be carried out more smoothly. Therefore, in measurement of exhalation, this device is more convenient to use and operate.

An exhalation measurement device with which zero point correction can be performed accurately, as well as a method for controlling this device may be provided.

DETAILED DESCRIPTION

Implementations of the exhalation measurement device will now be described through reference to the appended drawings.

1. Configuration

Overview of Exhalation Measurement Device

Figure 1:
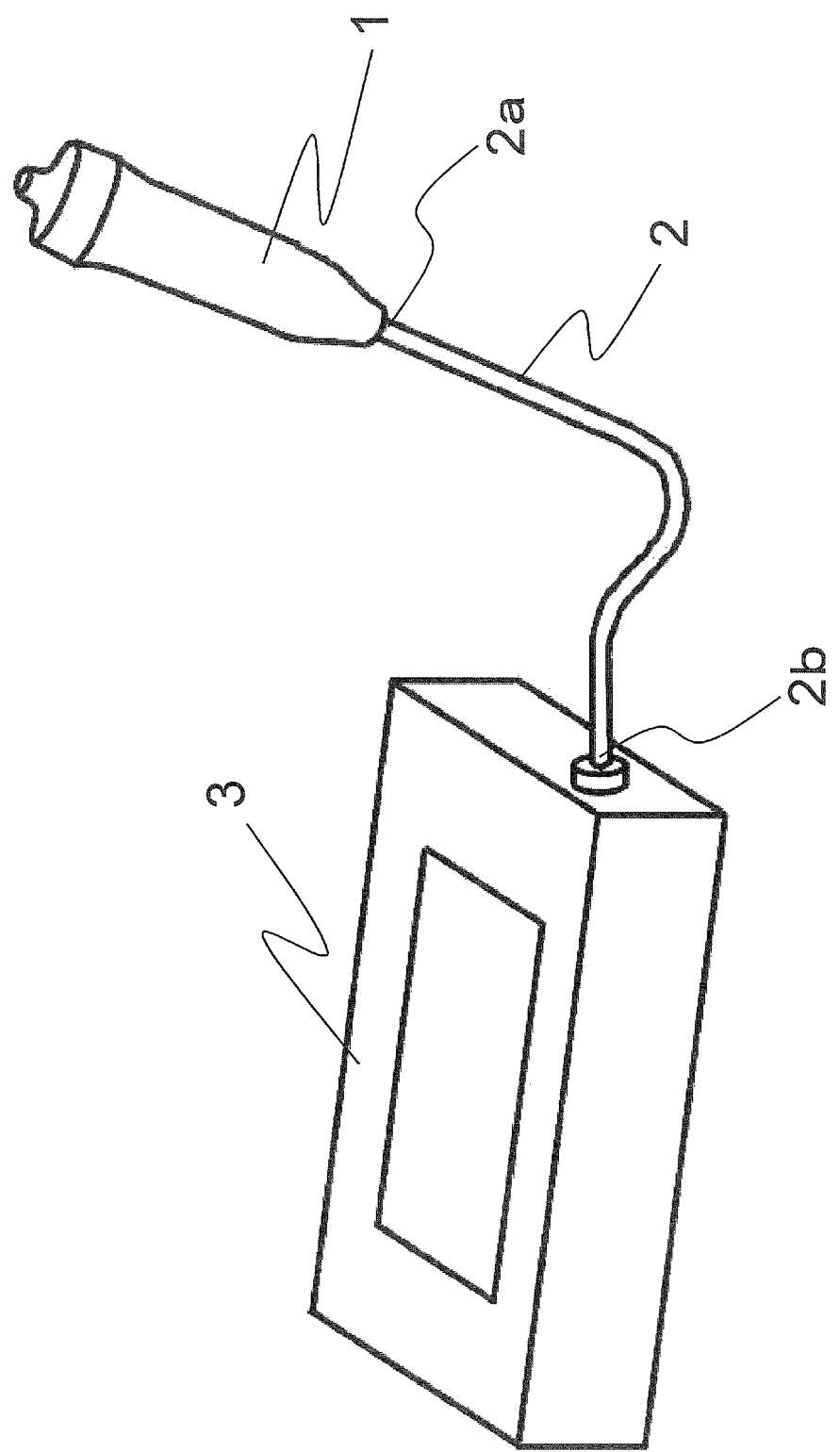
FIG. 1 is an oblique view of an exhalation measurement device.

FIG. 1 is an example of an exhalation measurement device, and shows an exhalation measurement device that measures nitrogen monoxide contained in exhalation, which is correlated to asthma diagnosis.

As shown in FIG. 1, the exhalation measurement device may comprise a handle component 1 and a measurement device main body 3 that is connected by a tube 2 to the handle component 1.

The handle component 1 is configured so that the user blows exhalation into the device through the handle component 1. One end 2a of the tube 2 is connected to this handle component 1, and the other end 2b of the tube 2 is connected to the measurement device main body 3, which is used to measure the exhalation that is blown in. That is, the handle component 1 is connected to the measurement device main body 3 via the tube 2.

Measurement Device Main Body 3

Figure 2:
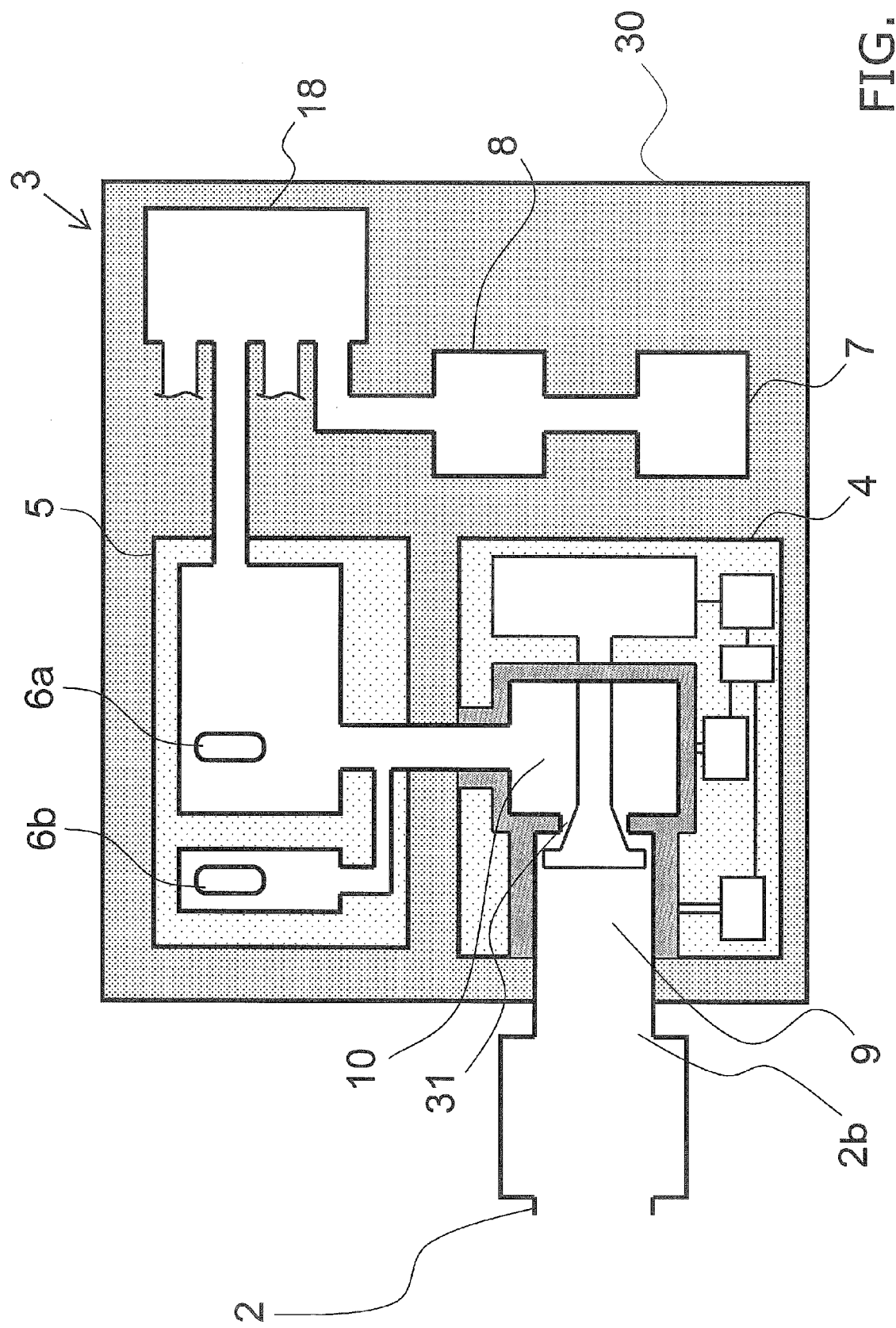
FIG. 2 shows the configuration of a measurement device main body in the exhalation measurement device in FIG. 1.

FIG. 2 shows a configuration of the measurement device main body 3 in the exhalation measurement device.

As shown in FIG. 2, the measurement device main body 3 has a flow regulator 4, a chamber 5, inlet/outlet holes 6a and 6b, a sensor 7, a pump 8, a switch valve 18, a main body case 30, and an open channel 60 (see FIGS. 6 to 9).

The flow regulator 4 is provided downstream from the handle component 1, and adjusts the flow of exhalation that is blown in from the handle component 1. The chamber 5 is provided downstream from the flow regulator 4, and temporarily holds the exhalation. The inlet/outlet holes 6a and 6b are through-holes provided to the chamber 5, and open up the flow regulator 4 to atmospheric pressure. The pump 8 is provided downstream from the chamber 5, and sends the exhalation held in the chamber 5 into the sensor 7. The switch valve 18 is provided between the chamber 5 and the pump 8, and sends the exhalation that is to be measured to the sensor 7, or sends gas that does not contain any nitrogen monoxide to the sensor 7 in order to initialize the sensor 7. The sensor 7 measures the amount of nitrogen monoxide contained in the exhalation that has been adjusted to a specific flow.

The above-mentioned flow regulator 4, chamber 5, inlet/outlet holes 6a and 6b, sensor 7, pump 8, and switch valve 18 are housed in the main body case 30.

Flow Regulator 4

Figure 3:
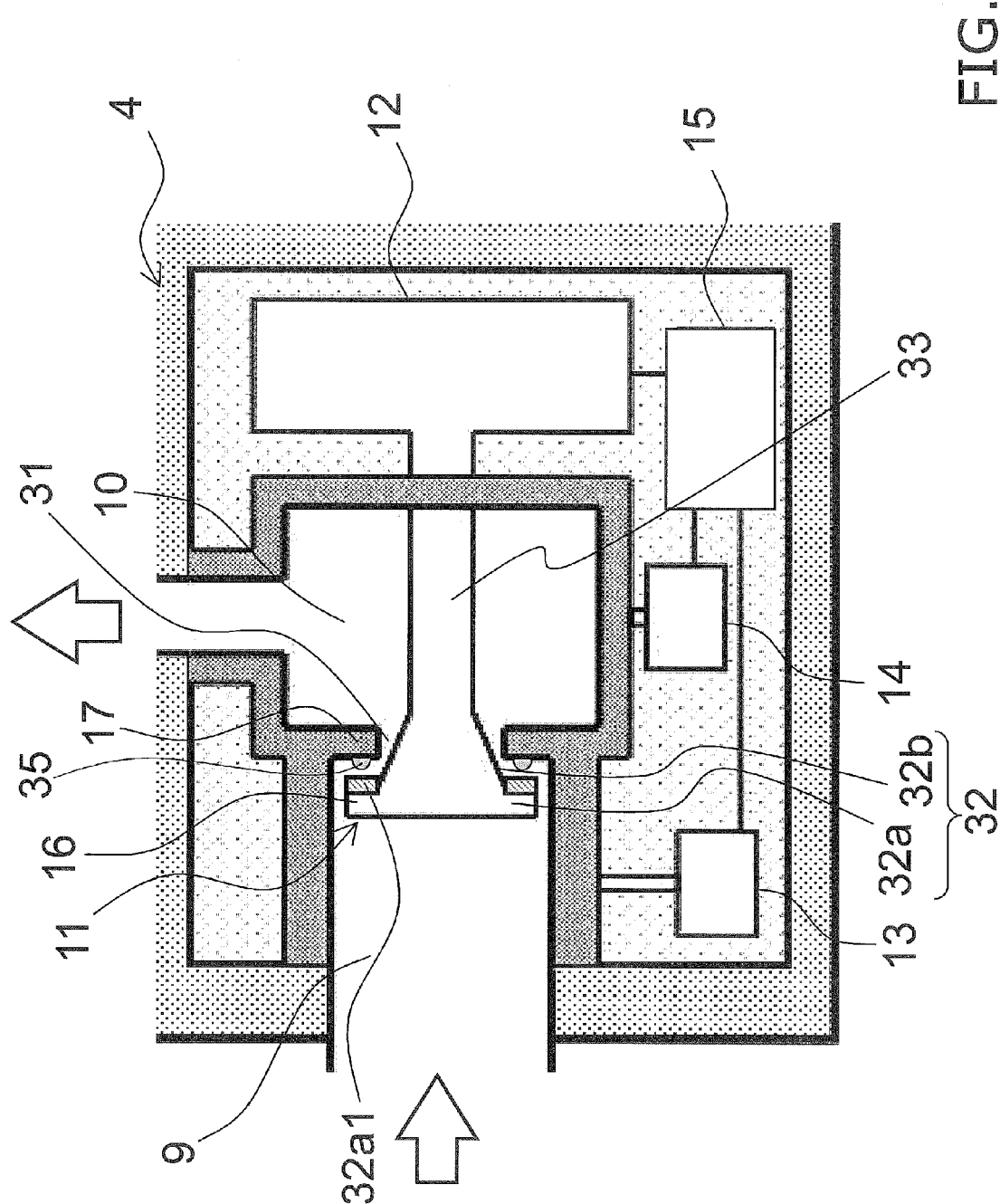
FIG. 3 shows the configuration of a flow regulator in the measurement device main body in FIG. 2.

FIG. 3 shows a configuration of the flow regulator. The flow regulator 4, which adjusts the flow of exhalation in order to measure the nitrogen monoxide contained in the exhalation, has an exhalation inflow component 9, an exhalation outflow component 10, an adjuster 11, a driver 12, an inflow pressure sensor 13, an outflow pressure sensor 14, and a flow regulator controller 15.

The exhalation inflow component 9 is connected to the end 2b of the tube 2, and allows exhalation to flow in from the handle component 1 side through the tube 2.

The exhalation outflow component 10 communicates with the exhalation inflow component 9 via a communicating hole 31, and is connected to the chamber 5. The exhalation that flows into the exhalation inflow component 9 flows out of the exhalation outflow component 10 to the chamber 5. Thus, the exhalation that flows into the flow regulator 4 goes through the exhalation inflow component 9 on the handle component 1 side and the exhalation outflow component 10 on the chamber 5 side, and flows out to the chamber 5.

Adjuster 11

The adjuster 11 is disposed along the path between the exhalation inflow component 9 and the exhalation outflow component 10, and adjust the flow of exhalation. The driver 12 moves the adjuster 11. More precisely, the adjuster 11 has a valve 32 and a shaft 33. The valve 32 is disposed in the exhalation inflow component 9, and is fixed through the communicating hole 31 to the shaft 33 that is disposed substantially perpendicular to the communicating hole 31. The shaft 33 is lined to the driver 12, and the driver 12 allows the shaft 33 to move in its axial direction.

The valve 32 has a disk-shaped first portion 32a and a truncated conical second portion 32b. The second portion 32b is provided to the face of the first portion 32a on the communicating hole 31 side. The second portion 32b is formed so that its diameter tapers from the exhalation inflow component 9 toward the exhalation outflow component 10. The second portion 32b is formed so that its largest diameter is smaller than the diameter of the first portion 32a. The shaft 33 is linked to the end of the second portion 32b on the exhalation outflow component 10 side.

The portion of the first portion 32a that protrudes past the second portion 32b forms a flange 16 on the valve 32. The flange 16 hits the wall 17 around the communicating hole 31, causing the communicating hole 31 to be blocked off by the valve 32 and separating the exhalation inflow component 9 and the exhalation outflow component 10. The flange 16 has an elastic member 32a1 formed from rubber or another such material on the communicating hole 31 side. This elastic member 32a1 is formed in a ring shape so as to surround the outside of the second portion 32b.

Meanwhile, a protrusion 35 that sticks out from the wall 17 toward the valve 32 is formed on the wall 17 around the communicating hole 31. This protrusion 35 is formed in a ring shape so as to surround the communicating hole 31.

In a state in which the communicating hole 31 has been closed by the valve 32 when the driver 12 moves the shaft 33 to the exhalation outflow component 10 side, the elastic member 32a1 is in contact with the protrusion 35 and the wall 17. When the valve 32 moves from a state of blocking the communicating hole 31 to the exhalation inflow component 9 side, this movement is accompanied by a gradually decrease in the diameter of the second portion 32b disposed in the communicating hole 31, so more exhalation moves from the exhalation inflow component 9 to the exhalation outflow component 10. Thus, the amount of exhalation moving from the exhalation inflow component 9 to the exhalation outflow component 10 can be gradually increased by having the valve 32 move to the exhalation inflow component 9 side.

The inflow pressure sensor 13 is disposed on the exhalation inflow component 9 side of the adjuster 11, and senses the pressure in the exhalation inflow component 9.

The outflow pressure sensor 14 is disposed on the exhalation outflow component 10 side of the adjuster 11, and senses the pressure in the exhalation outflow component 10.

The flow regulator controller 15 controls the driver 12.

Flow Regulator Controller 15

Figure 4:
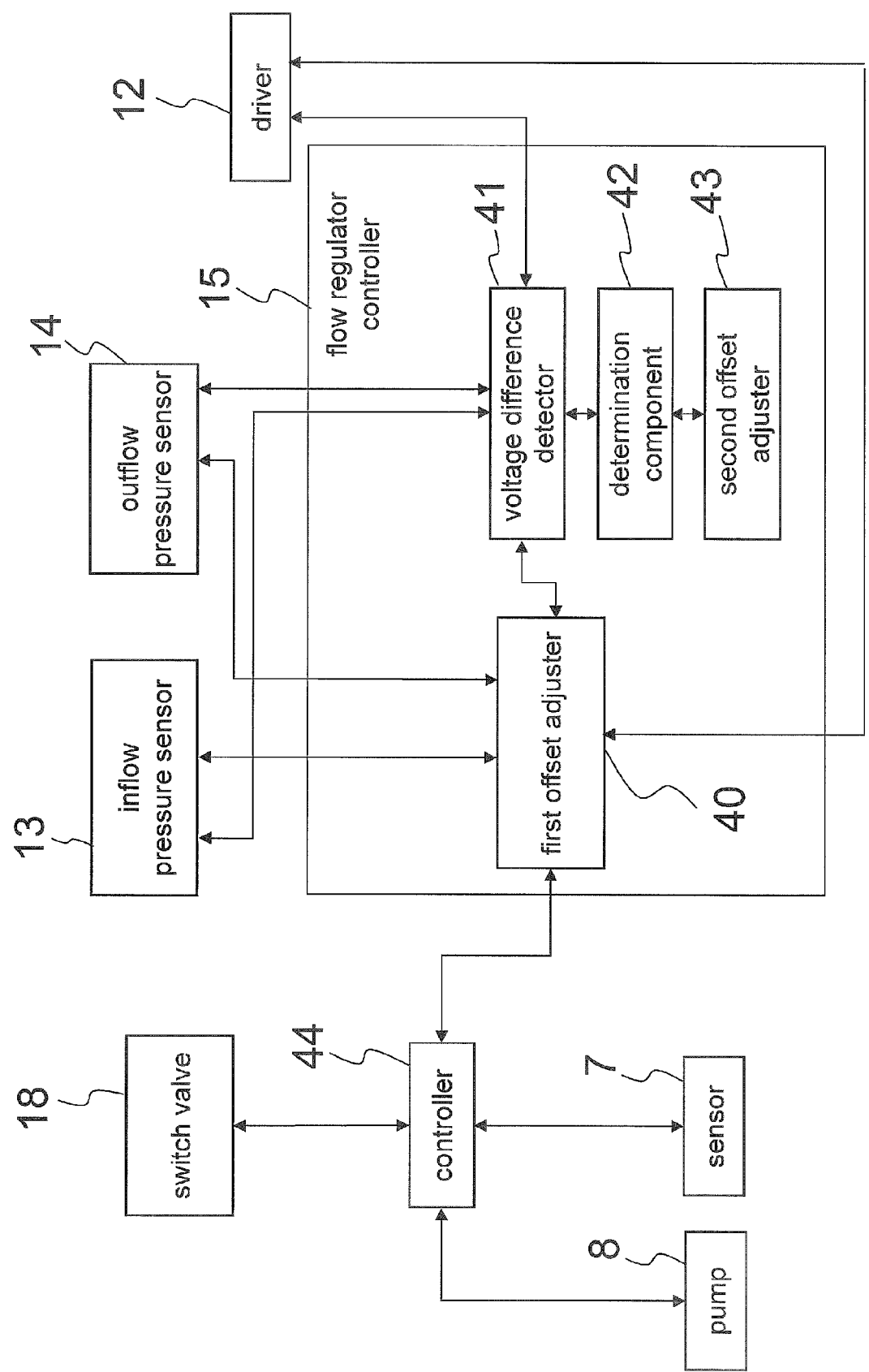
FIG. 4 shows the control configuration of the exhalation measurement device in FIG. 1.

FIG. 4 is a block diagram of an exhalation measurement device. As shown in FIG. 4, the flow regulator controller 15 has a first offset adjuster 40, a voltage difference detector 41, a determination component 42, and a second offset adjuster 43.

The first offset adjuster 40 separates the exhalation inflow component 9 from the exhalation outflow component 10 by moving the driver 12 to block off the communicating hole 31 with the valve 32, after which it adjusts the offset of the inflow pressure sensor 13 and the outflow pressure sensor 14 (an example of first offset adjustment).

The voltage difference detector 41 moves the driver 12 to separate the valve 32 from the wall 17, allowing the exhalation inflow component 9 to communicate with the exhalation outflow component 10. The voltage difference detector 41 calculates the difference in output voltage between the inflow pressure sensor 13 and the outflow pressure sensor 14, and detects the output voltage difference.

The determination component 42 determines whether or not to perform further offset adjustment on the inflow pressure sensor 13 on the basis of the output voltage difference found by the voltage difference detector 41. The determination component 42 determines not to perform further offset adjustment if the output voltage difference is substantially 0 (zero). The phrase "substantially 0 (zero)" here means that the difference in the output voltage between the inflow pressure sensor 13 and the outflow pressure sensor 14 is within the error range of each.

The second offset adjuster 43 performs offset adjustment of the inflow pressure sensor 13 using the output voltage difference if the determination component 42 has determined that second offset adjustment is to be performed (an example of second offset adjustment).

Chamber 5

Figure 5:
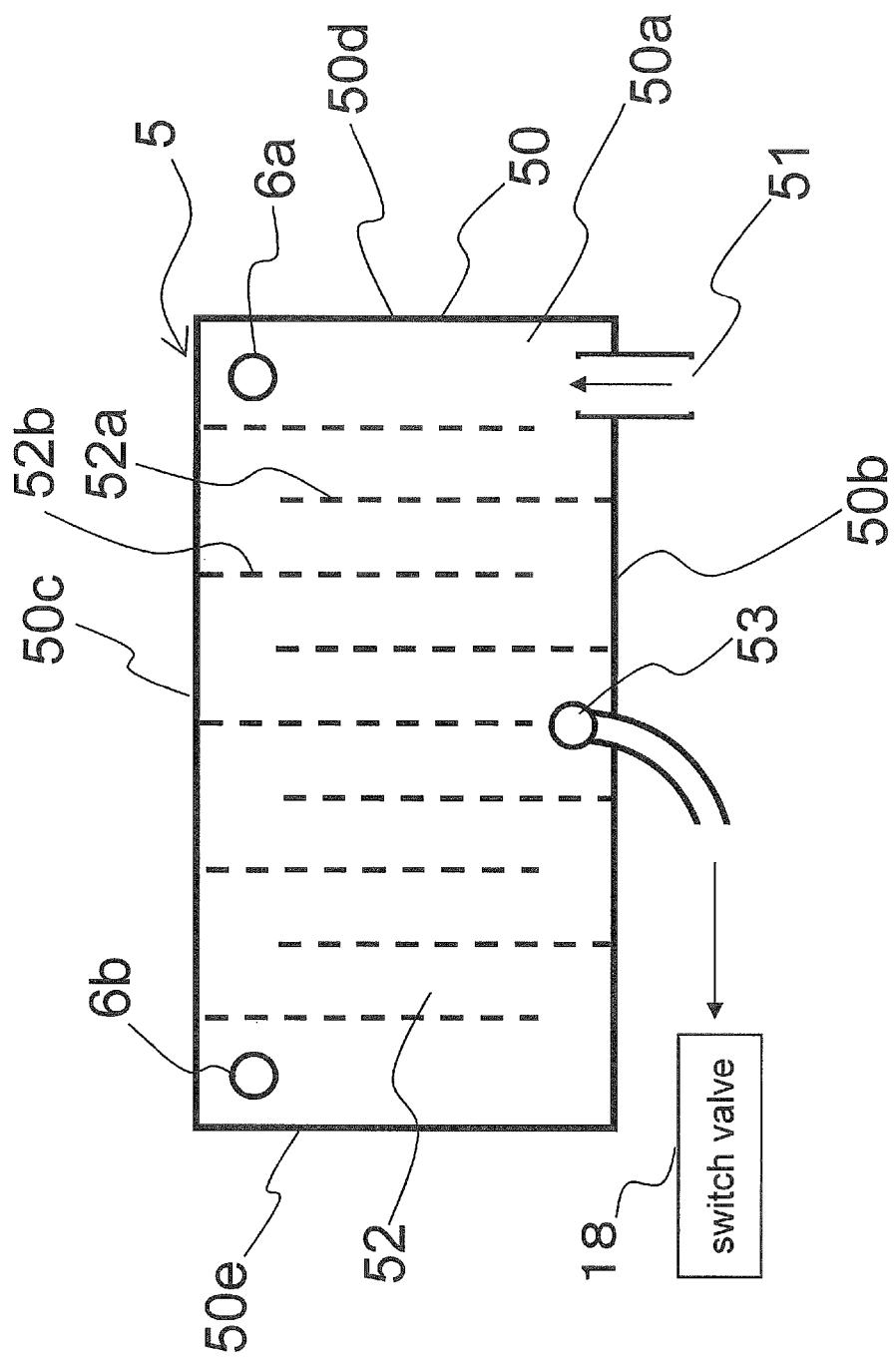
FIG. 5 is a plan view of the configuration of the chamber in FIG. 3.
Figure 6:
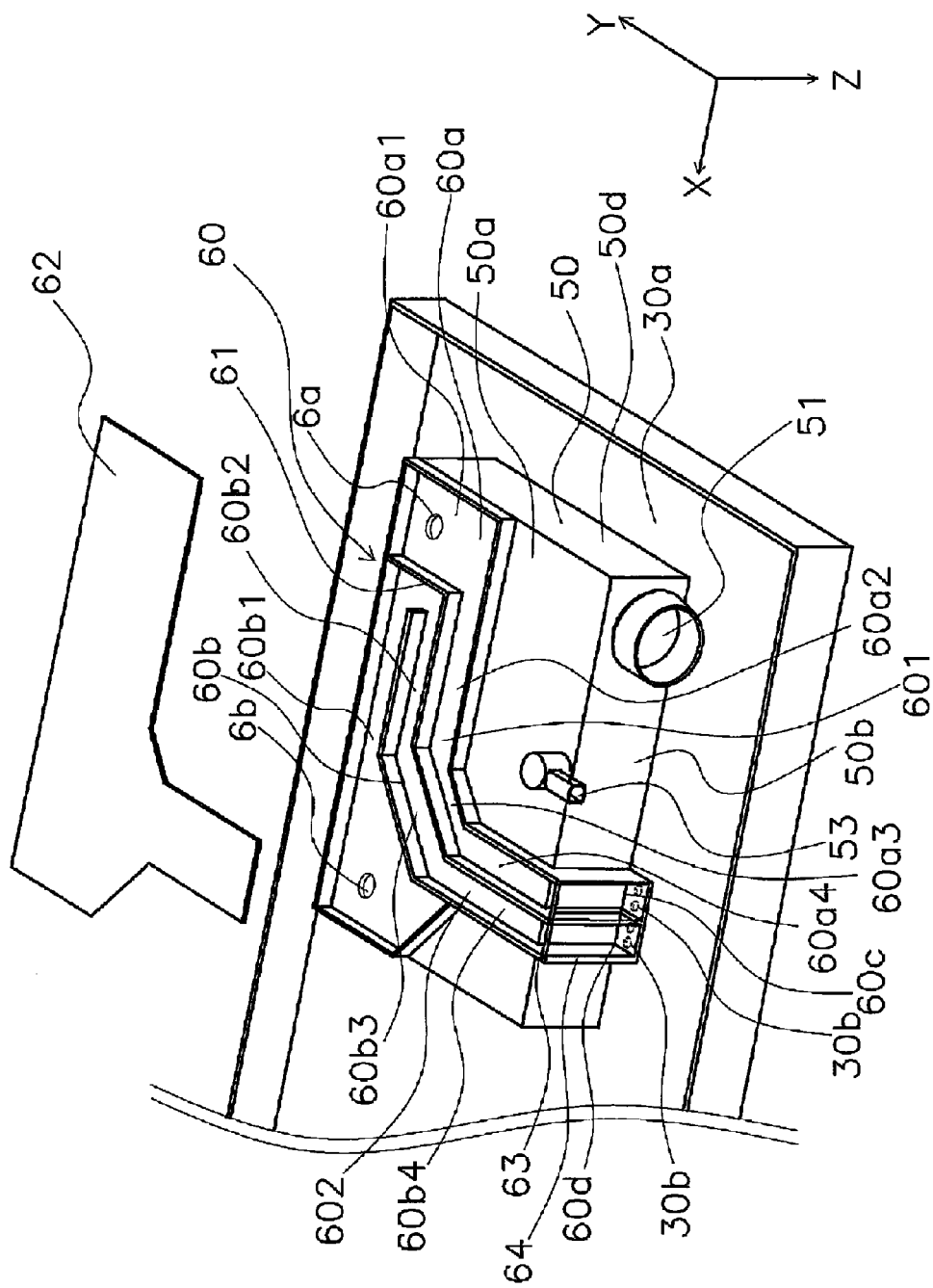
FIG. 6 is an oblique view of the chamber in FIG. 3.

FIG. 5 is a simplified diagram of the chamber 5. FIG. 6 is an external view of the chamber 5, and shows the state when a top plate 62 of the open channel 60 (discussed below) has been removed.

As shown in FIG. 5, the chamber 5 has a substantially cuboid container 50 and an inlet 51 from the flow regulator 4 that is formed in this container 50. As shown in FIG. 5, an undulating path 52 from the inlet 51 is formed in the interior of the container 50, and an outlet 53 to the switch valve 18 is formed in the middle portion of the undulating path 52. The inlet/outlet holes 6a and 6b are formed on the start and end point sides of the undulating path 52, respectively. The configuration of the undulating path 52 inside the chamber 5 is not shown in FIG. 2. The open channel 60 (discussed below) is formed on the upper face of the chamber 5 as shown in FIG. 6, but in FIG. 5 it is not shown so as to make the internal configuration of the chamber 5 easier to understand.

The positions of the inlet 51, the outlet 53, and the inlet/outlet holes 6a and 6b will be described in further detail below.

The substantially cuboid container 50 has opposing flat faces which are substantially rectangular, and side faces provided in between these flat faces and perpendicular to them.

The container 50 is fixed to the main body case 30 with one of the opposing flat faces touching the inner side of a face 30a of the main body case 30. In FIG. 6, of the opposing faces of the container 50, the face that is not touching the face 30a is numbered 50a. Actually, the main body case 30 is provided so as to house the entire chamber 5, but in FIG. 6, part of the main body case 30 (the upper portion in FIG. 1) is not shown in order to show the appearance of the chamber 5.

Also, as shown in FIG. 5, of the faces that are substantially perpendicular to the flat face 50a, the two that are linked to the long sides of the flat face 50a are numbered 50b and 50c, and the two that are linked to the short sides of the flat face 50a are numbered 50d and 50e. The side face 50b and the side face 50c are opposite each other, and the side face 50d and the side face 50e are opposite.

The undulating path 52 is formed by a plurality of flat walls 52a formed perpendicular to the flat face 50a from the side face 50b toward the side face 50c, and a plurality of flat walls 52b formed perpendicular to the flat face 50a from the side face 50c toward the side face 50b. The walls 52a and the walls 52b are disposed alternately from the side face 50d in the direction of the side face 50e.

The inlet 51 is provided to the end on the side face 50d side of the side face 50b.

The inlet/outlet holes 6a and 6b are through-holes formed in the flat face 50a. As shown in FIG. 5, the inlet/outlet hole 6a is provided near the corner of the side face 50c and the side face 50d. To put this another way, the inlet/outlet hole 6a is disposed at a position opposite the inlet 51. The inlet/outlet hole 6b is provided near the corner of the side face 50c and the side face 50e. The outlet 53 is disposed near the center of the long side, on the side face 50b side of the flat face 50a.

Open Channel 60

Figure 7:
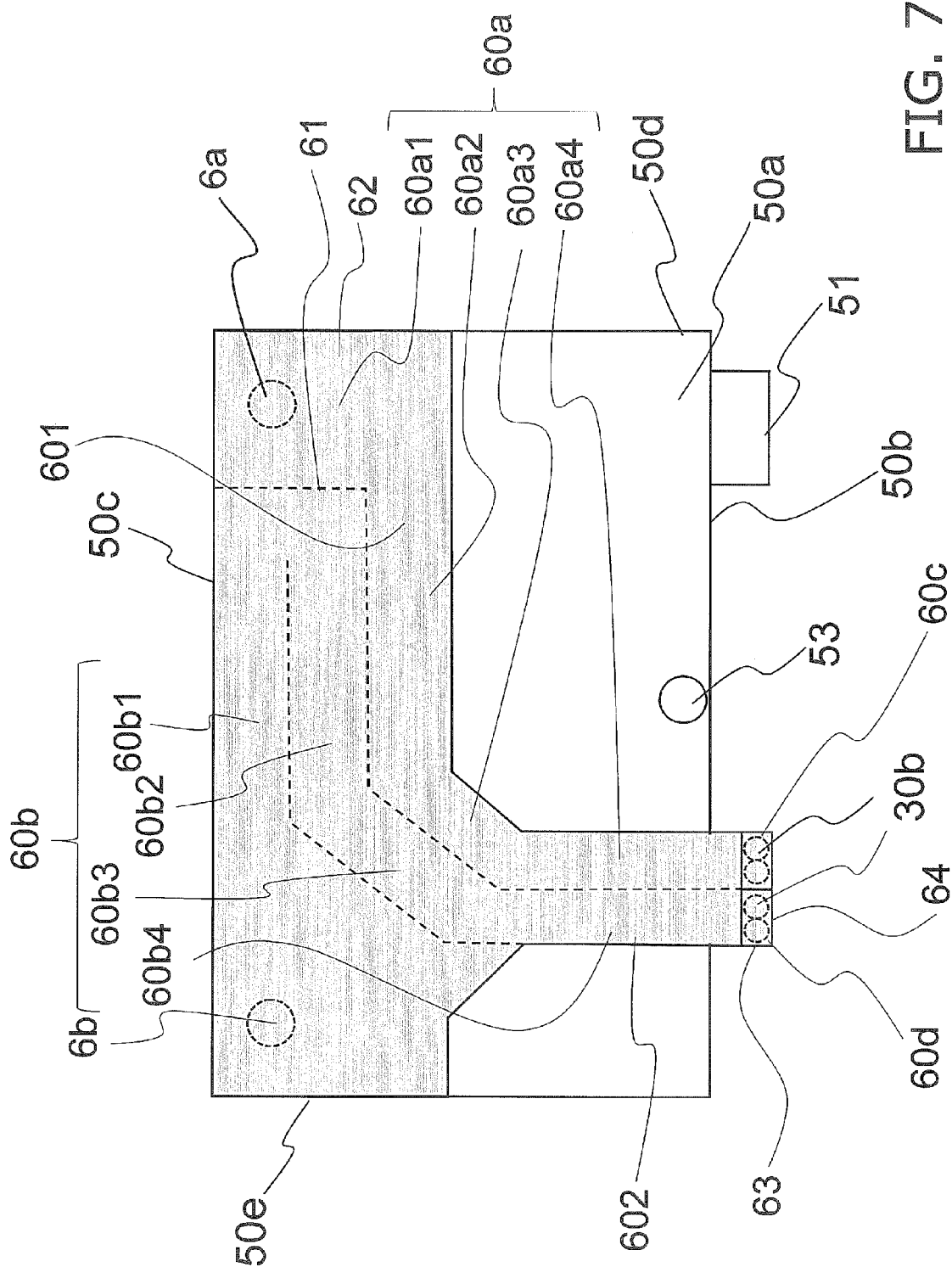
FIG. 7 is a plan view of an open channel formed on the surface of the chamber in FIG. 3.

FIG. 7 is a plan view of the open channel 60, and shows the chamber 5 as seen from above in FIG. 6.

As shown in FIGS. 6 and 7, four inlet/outlet holes 30b that connect the interior of the main body case 30 with the exterior are formed in the face 30a.

The open channel 60 connects the inlet/outlet holes 30b to the inlet/outlet holes 6a and 6b of the chamber 5. The open channel 60 has a channel A 601 that links the inlet/outlet hole 6a to two of the four inlet/outlet holes 30b (the right side in FIG. 7), and a channel B 602 that links the inlet/outlet hole 6b to the remaining two inlet/outlet holes 30b (the left side in FIG. 7).

More precisely, the channel A 601 has a first channel 60a that is linked to the inlet/outlet hole 6a, and a third channel 60c that links the first channel 60a and two of the inlet/outlet holes 30b (the right side in FIG. 7). The channel B 602 has a second channel 60b that is linked to the inlet/outlet hole 6b, and a fourth channel 60d that links the second channel 60b and the remaining two inlet/outlet holes 30b (the left side in FIG. 7).

The first channel 60a and the second channel 60b are formed in the flat face 50a, and the third channel 60c and the fourth channel 60d are formed in the side face 50b.

The first channel 60a and the second channel 60b are formed by the flat face 50a, a rib 61 provided sticking up from the flat face 50a, and a top plate 62 disposed so as to cover the rib 61.

The third channel 60c and the fourth channel 60d are formed by the side face 50b, a rib 63 provided sticking up from the side face 50b, and the top plate 64 disposed so as to cover the rib 63. The rib 61 and the rib 63 are linked.

The third channel 60c and the fourth channel 60d are disposed on the side face 50e side of the outlet 53, and are formed substantially perpendicular to the flat face 50a, from the flat face 50a toward the face 30a.

The first channel 60a has a first portion 60a1 that is formed from the inlet/outlet hole 6a toward the side face 50b, a second portion 60a2 that is formed from the distal end of the first portion 60a1 toward the side face 50e, a third portion 60a3 that is formed from the distal end of the second portion 60a2 toward the side face 50b, and a fourth portion 60a4 that is formed substantially perpendicular to the side face 50b from the distal end of the third portion 60a3 to the third channel 60c, toward the side face 50b.

The second channel 60b has a first portion 60b1 that is formed from the inlet/outlet hole 6b toward the side face 50d, a second portion 60b2 that is formed doubling back from the distal end of the first portion 60b1 toward the side face 50e, a third portion 60b3 that is formed from the distal end of the second portion 60b2 toward the side face 50b, and a fourth portion 60b4 that is formed from the distal end of the third portion 60b3 to the third channel 60c, toward the side face 50b.

Because the open channel 60 is thus formed so that the direction of gas flow changes, any changes in the outside atmosphere are less likely to be transmitted to the exhalation outflow component 10, so fluctuation in the sensing values of the outflow pressure sensor 14 caused by changes in the outside atmosphere can be suppressed.

Figure 8:
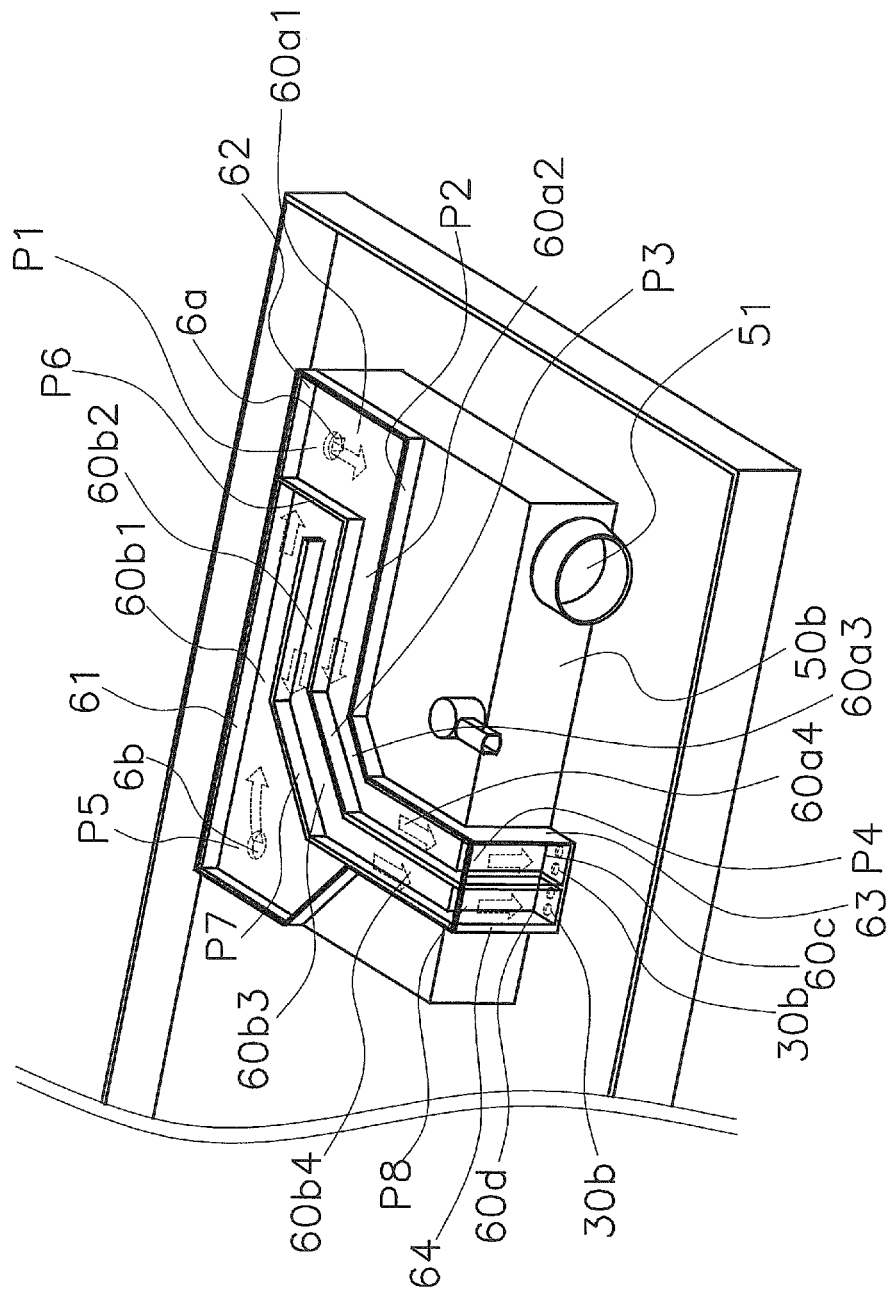
FIG. 8 is an oblique view of the chamber in FIG. 3.

More specifically, if fluctuation in the exterior pressure or the like causes the pressure in the interior to be higher than the exterior pressure, gas will flow out from the interior of the chamber 5. This state is shown in FIG. 8. The gas that has flowed out of the inlet/outlet hole 6a hits the top plate 62 (the P1 portion in FIG. 8), changes direction, and flows into the first portion 60a1. The gas flowing through the first portion 60a1 hits the rib 61 (the P2 portion in FIG. 8) at the curved portion of the second portion 60a2 from the first portion 60a1, changes direction, and flows into the second portion 60a2. The gas that flows through the second portion 60a2 hits the rib 61 (the P3 portion in FIG. 8) at the third portion 60a3, and changes direction, and flows into the forth portion 60a4. The gas that has flowed through the forth portion 60a4 and hit the top plate 64 (the P4 portion in FIG. 8) change direction, flows through the third channel 60c, and is discharged from the inlet/outlet hole 6b to the outside.

Also, the gas that has flowed out of the inlet/outlet hole 6b first hits the top plate 62 (the P5 portion in FIG. 8), changes direction, and flows into the first portion 60b1. The gas that flows through the first portion first portion 60b1 then hits the rib 61 (the P6 portion in FIG. 8) at the curved portion of the second portion 60b2 from the first portion 60b1, changes direction, and flows into the second portion 60b2. The gas that flows through the second portion 60b2 hits the rib 61 (the P7 portion in FIG. 8) at the third portion 60b3, changes direction, and flows into the fourth portion 60b4. The gas that has flowed through the fourth portion 60b4 and hit the top plate 64 (the P8 portion in FIG. 8) changes directions, flows through the fourth channel 60d, and is discharged from the inlet/outlet hole 6b to the outside.

Figure 9:
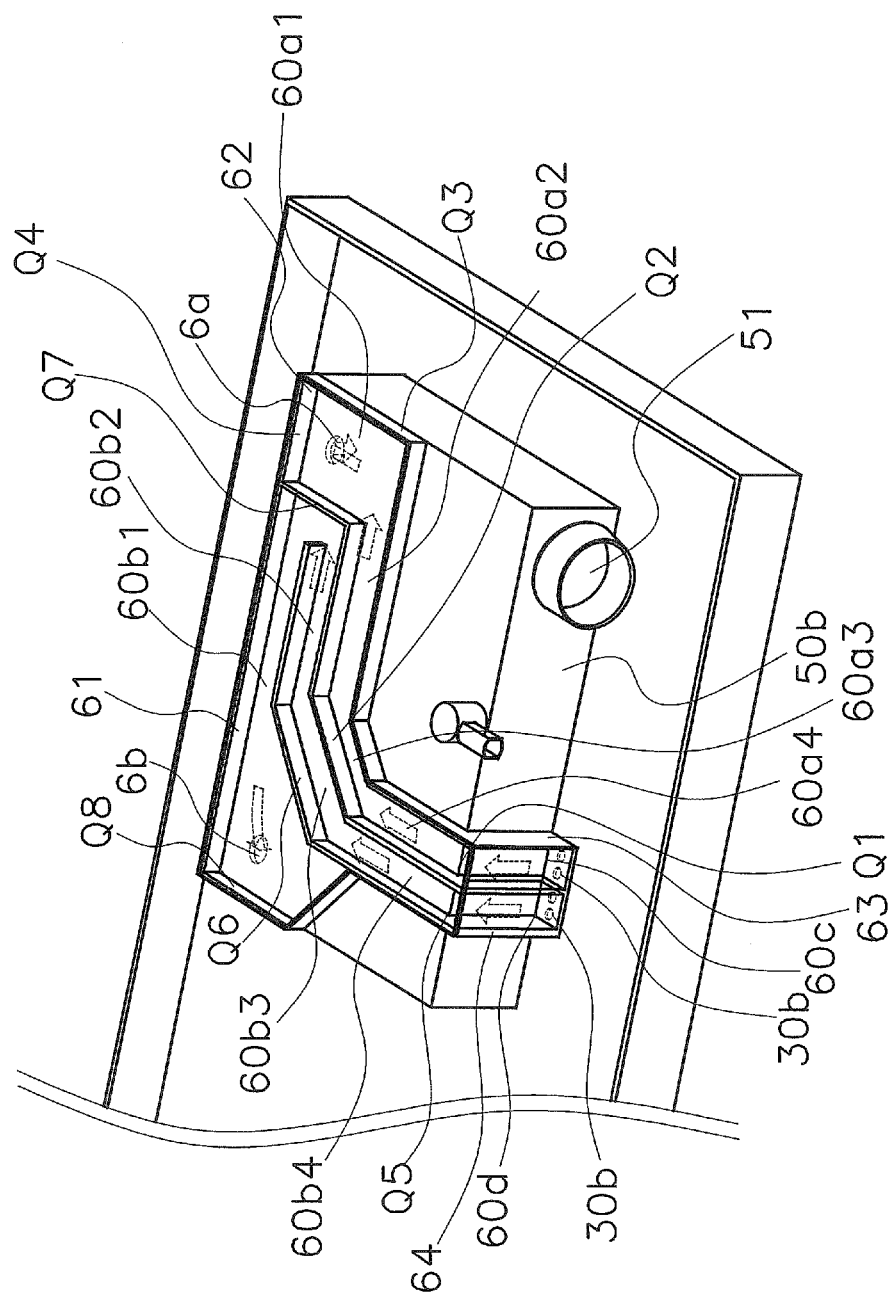
FIG. 9 is an oblique view of the chamber in FIG. 3.

Meanwhile, if the outside pressure increases, for example, gas (air) flows in from the outside. This state is shown in FIG. 9. The gas that has flowed in from the two inlet/outlet holes 30b on the right side in FIG. 9 flows through the third channel 60c, then hits the top plate 62 (the Q1 portion in FIG. 9), changes direction, and flows into the fourth portion 60a4. Then, the gas that flows through the fourth portion 60a4 hits the rib 61 (the Q2 portion in FIG. 9) at the third portion 60a3, changes direction, and flows into the second portion 60a2. The gas that flows through the second portion 60a2 hits the rib 61 (the Q3 portion in FIG. 9) at the curved part of the first portion 60a1 and the second portion 60a2, changes direction, and flows into the first portion 60a1. Then, the gas that has flowed through the first portion 60a1 and hit the rib 61 (the Q4 portion in FIG. 9) changes direction and flows into the inlet/outlet hole 6b.

The gas that has flowed from the two inlet/outlet holes 30b on the left side in FIG. 6 flows through the fourth channel 60d and then hits the top plate 62 (the Q5 portion in FIG. 9), changes direction, and flows into the fourth portion 60b4. The gas that flows through the fourth portion 60b4 then hits the rib 61 (the Q6 portion in FIG. 9) at the third portion 60b3, changes direction, and flows into the second portion 60b2. The gas that flows through the second portion 60b2 hits the rib 61 (the Q7 portion in FIG. 9) at the curved part of the first portion 60b1 and the second portion 60b2, changes direction, and flows into the first portion 60b1. The gas that flows through the first portion 60b1 and hits the rib 61 (the Q8 portion in FIG. 9) then changes direction and flows into the inlet/outlet hole 6b.

In the description of FIGS. 8 and 9, only the main portions out of the portions where the gas hits and changes direction are discussed, but actually the gas hits all of the portions in the channel. For instance, in FIG. 8, the gas that has hit the P4 portion flows into the inlet/outlet holes 30b while in contact with the Q1 portion shown in FIG. 9. Also, in FIG. 9, the gas that has hit the Q4 portion flows into the inlet/outlet hole 6a while in contact with the P1 portion shown in FIG. 8.

Thus, both when gas which exits the chamber 5 goes outside the measurement device main body 3, and when gas flows into the chamber 5 form the outside, the gas cannot move in or out unless it changes its direction while in contact with the ribs 61 and 63 or the top plates 62 and 64, so fluctuations in the gas are not transmitted directly to the interior of the chamber 5, and their effect on the interior can be diminished.

Also, wall portions (such as the P1, P4, Q1, and Q4 portions) that make up the open channel 60 are formed at least at positions opposite the inlet/outlet holes 6a and 6b, or at positions opposite the inlet/outlet holes 30b. Therefore, when gas moves from the inlet/outlet holes 6a and 6b toward the inlet/outlet holes 30b, or when gas moves from the inlet/outlet holes 30b toward the inlet/outlet holes 6a and 6b, the gas will hit these walls and the direction of its flow will be greatly changed, so any external effect can be prevented from directly affecting the interior of the chamber 5.

As shown in FIG. 4, the exhalation measurement device may comprise a controller 44 that controls the switch valve 18, the pump 8, and the sensor 7. This controller 44 is connected to the flow regulator controller 15, and controls the switch valve 18 by receiving signals from the first offset adjuster 40, for example.

2. Operation

Figure 10:
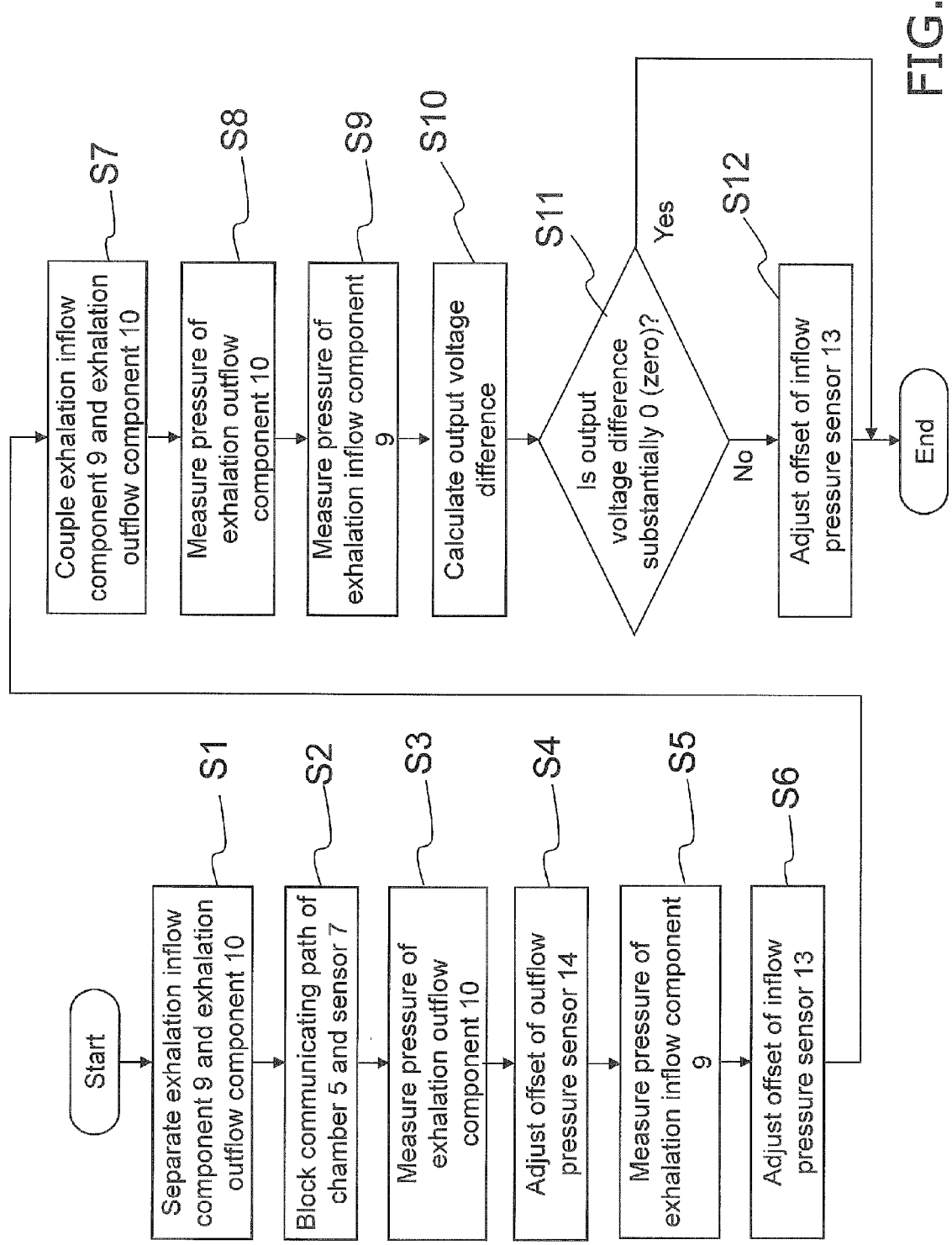
FIG. 10 is a flowchart of the control operation of the exhalation measurement device in FIG. 1.

When a user uses an exhalation measurement device configured as above to measure the nitrogen monoxide content in exhalation, zero point correction of the outflow pressure sensor 14 and the inflow pressure sensor 13 that make up the flow regulator 4 is performed prior to exhalation measurement, using a signal to start measurement, such as switching on the power to the exhalation measurement device, as a trigger. FIG. 10 is a flowchart of the control operation in zero point correction of an implementation of an exhalation measurement device.

This zero point correction will now be described through reference to FIGS. 2 to 10.

The first offset adjuster 40 of the flow regulator controller 15 uses the above-mentioned trigger to move the adjuster 11 prior to measuring the nitrogen monoxide content in the exhalation, which causes the flange 16 of the adjuster 11 to hit the wall 17 formed between the exhalation inflow component 9 and the exhalation outflow component 10. This puts the exhalation inflow component 9 and the exhalation outflow component 10 into a separated state.

The linking path of the chamber 5 and the sensor 7 (pump 8) is temporarily blocked off by the switch valve 18 (S2). In S2, a movement completion signal is sent from the first offset adjuster 40 to the controller 44 upon completion of the movement of the adjuster 11 in S1, and the controller 44 controls the blocking produced by the switch valve 18.

The first offset adjuster 40 uses the inflow pressure sensor 13 and the outflow pressure sensor 14 to measure the pressure of the exhalation inflow component 9 and the exhalation outflow component 10 in a state in which the exhalation inflow component 9 and the exhalation outflow component 10 have been separated, these first measurement results are outputted to the first offset adjuster 40, and offset adjustment of the inflow pressure sensor 13 and the outflow pressure sensor 14 is performed (S3 to S6).

Here, the inlet/outlet holes 6a and 6b that open up to atmospheric pressure are provided to the chamber 5 linked to the exhalation outflow component 10 in order to keep the pressure constant in the interior. Since the linking path in the direction of the sensor 7 (the pump 8) is blocked off by the switch valve 18 disposed downstream from the chamber 5, the exhalation outflow component 10 and the chamber 5 are at atmospheric pressure.

In this state (in which the exhalation outflow component 10 is under an atmospheric pressure environment), the pressure of the exhalation outflow component 10 is measured, this measurement result is outputted to the first offset adjuster 40 (S3), and the first offset adjuster 40 performs offset adjustment on the outflow pressure sensor 14 on the basis of the outputted measurement result (S4).

Next, the pressure of the exhalation inflow component 9 is measured, this measurement result is outputted to the first offset adjuster 40 (S5), and the first offset adjuster 40 performs offset adjustment on the inflow pressure sensor 13 on the basis of the outputted measurement result (S6).

Next, the voltage difference detector 41 moves the adjuster 11 to create a state in which the exhalation inflow component 9 and the exhalation outflow component 10 are coupled (also called "linked") (S7).

After this, the inflow pressure sensor 13 and the outflow pressure sensor 14 are used to measure the pressure of the exhalation inflow component 9 and the exhalation outflow component 10, and the second measurement result is outputted to the voltage difference detector 41 (S8 and S9).

The above-mentioned first measurement result and second measurement result are used to perform zero point correction on the inflow pressure sensor 13 and the outflow pressure sensor 14.

The above-mentioned steps S3 to S9 will now be described in detail through reference to FIG. 11.

Figure 11:
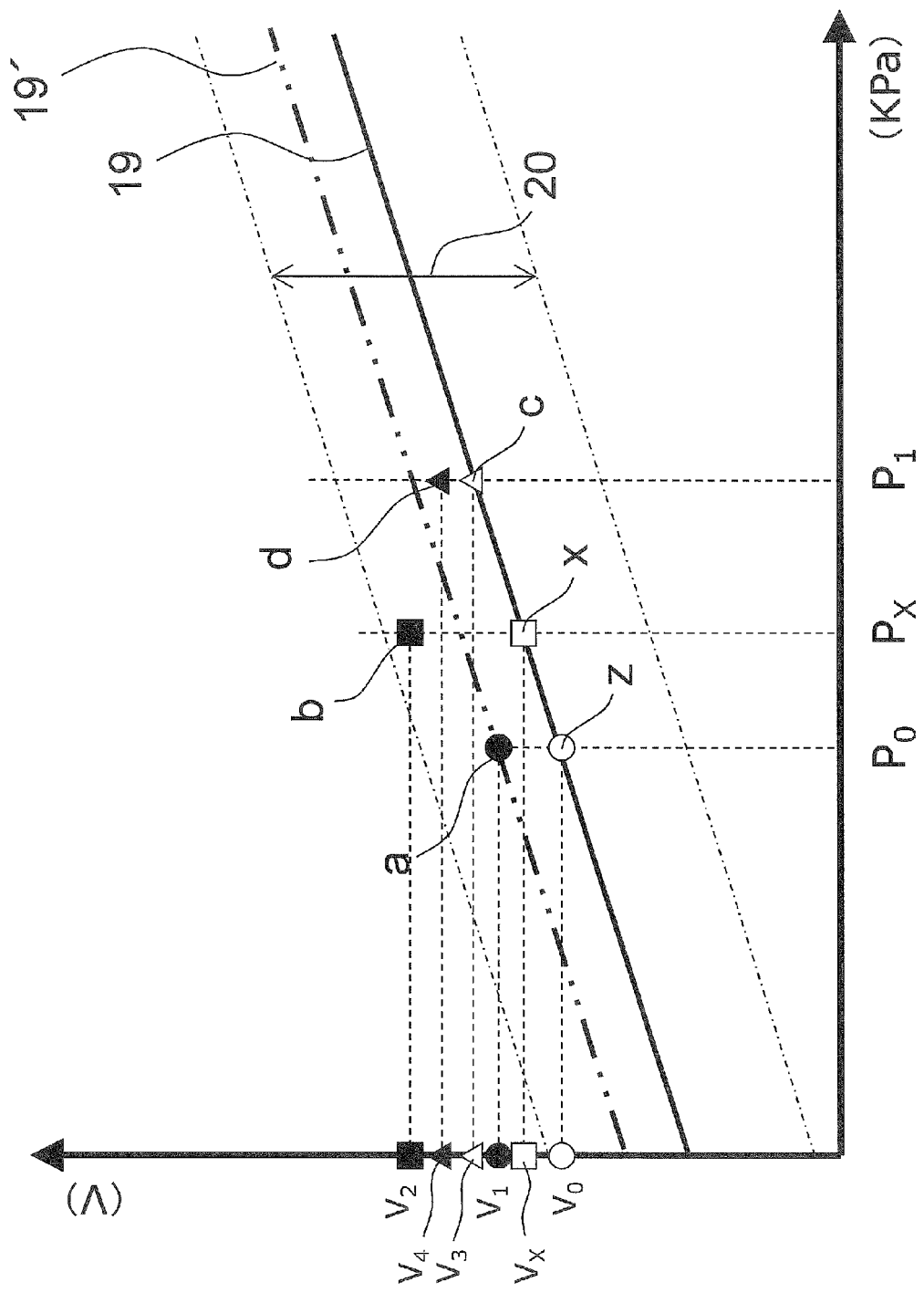
FIG. 11 is a graph of the relation between output voltage and the pressure of a pressure sensor.

In FIG. 11, the line 19 shows the reference characteristics of a pressure sensor, and 20 is the offset range. The term "reference characteristics" here means the output voltage theoretically outputted by the pressure sensor under a specific known pressure environment, while "offset range" means the variance width over which the pressure sensor outputs its output voltage under a specific known pressure environment.

The inflow pressure sensor 13 and the outflow pressure sensor 14 may be of the same type of pressure sensor, having the reference characteristics (line 19) and offset range 20 shown in FIG. 11, and FIG. 11 will be used to describe zero point correction of the inflow pressure sensor 13 and the outflow pressure sensor 14.

First, in a state in which the exhalation inflow component 9 and the exhalation outflow component 10 have been separated, the pressure of the exhalation outflow component 10 is measured by the outflow pressure sensor 14 (S3). The pressure of the exhalation outflow component 10 here is atmospheric pressure ($P_0$), so the output voltage is supposed to be outputted as $V_0$ (point z) from the reference characteristics of the outflow pressure sensor 14. Nevertheless, the actual measured value is outputted as an output voltage $V_1$ (point a). In theory, under a known pressure environment of atmospheric pressure ($P_0$), the output voltage needs to be outputted as $V_0$ (point z), so offset adjustment of the reference characteristics is performed so that the output voltage that is outputted at atmospheric pressure ($P_0$) will go from $V_1$ to $V_0$ (S4).

Specifically, in a state before offset adjustment is performed, the characteristics of the outflow pressure sensor 14 are indicated by the line 19'. The line 19' can be expressed as $y=ax+b_1$ (x and y are variables). Since $a \times P_0 + b_1 = V_1$ here, offset adjustment is performed to the reference characteristics of the outflow pressure sensor 14 as $y=ax+b_1+(V_0-V_1)$ so as to indicate the value of $V_0$ in the case of $P_0$. Specifically, the characteristics of the outflow pressure sensor 14 can be matched to the reference characteristics (line 19) by moving an intercept by $(V_0-V_1)$ in a state in which the slope is the same with respect to the line 19'.

Next, the pressure of the exhalation inflow component 9 is measured by the inflow pressure sensor 13 in a state in which the exhalation inflow component 9 and the exhalation outflow component 10 have been separated (S5). The exhalation inflow component 9 is linked to the handle component 1, which has an inlet that is always open and is used to blow in exhalation. Therefore, unlike with the exhalation outflow component 10, the pressure $(P_x)$ of the exhalation inflow component 9 is uncertain. The pressure of the exhalation inflow component 9 is measured using the inflow pressure sensor 13 under this pressure environment $(P_x)$, and as a result the output voltage is $V_2$ (point b). Here, the output voltage $V_2$ is assumed to be a value when the pressure is under an atmospheric pressure $(P_0)$ environment, and offset adjustment is performed so that the output voltage $V_0$ is outputted instead of the output voltage $V_2$ (S6).

More specifically, since the reference characteristics of the inflow pressure sensor 13 are also indicated by the line 19, if we let the characteristics of the inflow pressure sensor 13 before offset adjustment be $y=ax+b_2$, then offset adjustment of the inflow pressure sensor 13 is performed as $y=ax+b_2+(V_0-V_2)$.

As discussed above, the inflow pressure sensor 13 and the outflow pressure sensor 14 are used to measure the pressure of the exhalation inflow component 9 and the exhalation outflow component 10 in a state in which the exhalation inflow component 9 and the exhalation outflow component 10 have been separated (S3 and S5), and offset adjustment is performed so that the output voltage $V_0$ is outputted instead of the output voltage $V_1$ and the output voltage $V_2$ (S4 and S6) (an example of first offset adjustment).

Next, the voltage difference detector 41 moves the adjuster 11 to create a state in which the exhalation inflow component 9 and the exhalation outflow component 10 are coupled (also called "communicating") (S7). In this coupled state, the inflow pressure sensor 13 and the outflow pressure sensor 14 are used to measure the pressure of the exhalation inflow component 9 and the exhalation outflow component 10 (S8 and S9).

Here, since the exhalation inflow component 9 and exhalation outflow component 10 are in a coupled state, they have the same pressure value, and this pressure value is shown in FIG. 11 as $P_1$. In a state in which the exhalation inflow component 9 and the exhalation outflow component 10 are coupled, the proper offset adjustment is performed on the outflow pressure sensor 14 in S4, so the output voltage that is outputted by the outflow pressure sensor 14 in S8 is $V_3$ (the point c) from the reference characteristics (the line 19), as shown in FIG. 11.

Meanwhile, the output voltage that is outputted by the inflow pressure sensor 13 in S9 is assumed to be a value at which the output voltage $(V_2)$ is under an atmospheric pressure $(P_0)$ environment, and first offset adjustment is performed, so it is unclear whether or not it is outputted as the output voltage $V_3$.

Therefore, it is determined whether or not the output voltage (Vs) that is outputted by the inflow pressure sensor 13 is the same as the output voltage $(V_3)$ of the outflow pressure sensor 14 (S10 and S11).

After the pressure measurement of the exhalation inflow component 9 has been performed by the inflow pressure sensor 13 in S9, the voltage difference detector 41 finds the difference between the output voltage (Vs) of the inflow pressure sensor 13 obtained in S9 and the output voltage $(V_3)$ of the outflow pressure sensor 14 obtained in S8 (S10).

Next, the determination component 42 determines whether or not the output voltage difference $(Vs-V_3)$ found in S10 is substantially 0 (zero) (S11). Specifically, it is determined whether or not the output voltage (Vs) of the inflow pressure sensor 13 is substantially the same as the output voltage $(V_3)$ of the outflow pressure sensor 14 (S11). Here, the output voltage (Vs) of the inflow pressure sensor 13 need only be substantially the same as the output voltage $(V_3)$ of the outflow pressure sensor 14, and need not be exactly the same. The terms "substantially the same" and "substantially 0 (zero)" may refer to a permissible range that varies with the specifications of the device and the error range of the output voltage.

The output voltage Vs that is outputted by the inflow pressure sensor 13 will now be described for a case in which it is outputted as the output voltage $V_3$.

If the output voltage Vs of the inflow pressure sensor 13 is outputted as the output voltage $V_3$ (if the output voltage difference is determined to be zero), then the first offset adjustment of the inflow pressure sensor 13 can be concluded to have been performed so as to obtain the reference characteristics (the line 19), just as with the outflow pressure sensor 14.

Therefore, the pressure of the exhalation inflow component 9 in a state in which the exhalation inflow component 9 and the exhalation outflow component 10 have been separated can be concluded to be atmospheric pressure $(P_0)$. That is, the inflow pressure sensor 13 completes correction to the reference characteristics (the line 19) by means of first offset adjustment, and control of the zero point correction is ended.

However, if the output voltage (Vs) of the inflow pressure sensor 13 is not outputted as the output voltage $(V_3)$, but as $V_4$, the pressure (Px) of the exhalation inflow component 9 in a state in which the exhalation inflow component 9 and the exhalation outflow component 10 have been separated can be concluded not to be atmospheric pressure $(P_0)$. That is, correction to the reference characteristics (the line 19) of the inflow pressure sensor 13 is not completed with first offset adjustment.

In view of this, second offset adjustment is performed using the difference between the output voltage $(V_4)$ of the inflow pressure sensor 13 and the output voltage $(V_3)$ of the outflow pressure sensor 14, and correction to the reference characteristics (the line 19) of the inflow pressure sensor 13 is completed (S12).

Specifically, correction to the reference characteristics (the line 19) can be completed by further subjecting the inflow pressure sensor 13 to offset adjustment following the first offset adjustment, according to the difference between the output voltage $(V_4)$ and the output voltage $(V_3)$.

More specifically, after the first offset adjustment, the characteristics of the inflow pressure sensor 13 are adjusted to be $y=ax+b_2+(V_0-V_2)$. Then, since the exhalation inflow component 9 and the exhalation outflow component 10 are communicating, they both have the same pressure value $P_1$. The output voltage of the outflow pressure sensor 14 at this pressure value $(P_1)$ is $V_3$. At the pressure value $(P_1)$, the output voltage of the inflow pressure sensor 13 is $V_4$. Therefore, correction should be performed so that the output voltage of the inflow pressure sensor 13 will be $V_3$, so the inflow pressure sensor 13 can be set to the reference characteristics (the line 19) by adjusting to $y=ax+b_2+(V_0-V_2)+(V_3-V_4)$.

As discussed above, in a state in which the exhalation inflow component 9 and the exhalation outflow component 10 are coupled, the inflow pressure sensor 13 and the outflow pressure sensor 14 are used to measure the pressure of the exhalation inflow component 9 and the exhalation outflow component 10, and if the result of comparing the output voltage Vs and the output voltage $V_3$ is that they are the same (if the output voltage Vs is substantially $V_3$), then the state of the first offset adjustment is maintained, but if the comparison results are different (if the output voltage Vs is $V_4$), then further offset adjustment (second offset adjustment) is performed using the difference between the above-mentioned output voltage ($V_4$) and the output voltage ($V_3$) with respect to the characteristics after the first offset adjustment was performed.

Therefore, even if the environment before the start of measurement should change significantly, zero point correction of the inflow pressure sensor 13 and the outflow pressure sensor 14 for adjusting the flow can be carried out accurately, without being affected by the environment.

That is, since first offset adjustment is performed, and second offset adjustment is performed using the difference in the output voltages between the exhalation inflow component 9 and the exhalation outflow component 10, even if there is a change over time, zero point correction of the inflow pressure sensor 13 and the outflow pressure sensor 14 will always be possible under an atmospheric pressure environment during measurement, the effect of changes over time can be suppressed, and the flow established as a guideline can be accurately controlled.

Therefore, since the exhalation that is blown in can be stably kept in the chamber 5, it is less likely that measurement will be impossible, and the inconvenience of having to repeat measurement, etc., can be eliminated. This means that it is more convenient for a user to take exhalation measurements.

3. Main Features
3-1

The exhalation measurement device may comprise the handle component 1, the flow regulator 4, the chamber 5, the inlet/outlet holes 6a and 6b (an example of first through-holes), the sensor 7 (an example of a measurement component), and the pump 8. Exhalation is blown into the handle component 1. The flow regulator 4 is provided downstream from the handle component 1 and adjusts the flow of exhalation blown in from the handle component 1. The chamber 5 is provided downstream from the flow regulator 4 and temporarily stores exhalation. The inlet/outlet holes 6a and 6b are provided to the chamber 5 and opens up the flow regulator 4 to atmospheric pressure. The sensor 7 measures a specific component in exhalation. The pump 8 is provided downstream from the chamber 5 and sends exhalation into the sensor 7.

The flow regulator 4 has the exhalation inflow component 9, the exhalation outflow component 10, the adjuster 11 (an example of a flow adjuster), the driver 12, the inflow pressure sensor 13, the outflow pressure sensor 14, the first offset adjuster 40, the voltage difference detector 41, and the second offset adjuster 43. The exhalation inflow component 9 is where exhalation flows in from the handle component 1 side. The exhalation outflow component 10 is where exhalation flows out to the chamber 5 side. The adjuster 11 is provided between the exhalation inflow component 9 and the exhalation outflow component 10 and adjusts the flow of exhalation. The driver 12 moves the flow adjuster 11. The inflow pressure sensor 13 senses the pressure of the exhalation inflow component 9. The outflow pressure sensor 14 senses the pressure of the exhalation inflow component 10. The first offset adjuster 40 causes the driver 12 to move the flow adjuster 11 and create a separated state between the exhalation inflow component 9 and the exhalation outflow component 10, and performs first offset adjustment of the inflow pressure sensor 13 and the outflow pressure sensor 14. The voltage difference detector 41 causes the driver to move the flow adjuster 11 and create a linked state between the exhalation inflow component 9 and the exhalation outflow component 10, and detects the output voltage difference after the first offset adjustment of the inflow pressure sensor 13 and the outflow pressure sensor 14. The second offset adjuster 43 uses the output voltage difference to perform second offset adjustment of the inflow pressure sensor 13.

As discussed above, after first offset adjustment is performed, second offset adjustment is performed using the difference in output voltage between the inflow pressure sensor 13 and the outflow pressure sensor 14.

Specifically, in the second offset adjustment, since the exhalation inflow component 9 and the exhalation outflow component 10 are linked, they are both at the same pressure. Therefore, second offset adjustment of the inflow pressure sensor 13 can be performed on the basis of the value of the outflow pressure sensor 14 that has undergone suitable zero point correction in the first offset adjustment.

Therefore, even if gas flows into the exhalation inflow component 9 from the handle component 1 side, or if gas flows out from the exhalation inflow component 9 side to the handle component 1 side, zero point correction can be properly performed on the inflow pressure sensor 13.

Also, when these offset adjustments are performed before measurement, even if there are changes over time, zero point correction of the inflow pressure sensor 13 and the outflow pressure sensor 14 will always be possible under an atmospheric pressure environment during measurement, so the measurement will not be affected by changes over time, and the flow established as a guideline can be accurately controlled.

3-2

With the exhalation measurement device, the exhalation outflow component 10 may be in a separated state is under an atmospheric pressure environment, and the first offset adjuster 40 performs first offset adjustment so that the value sensed by the outflow pressure sensor 14 is atmospheric pressure.

Consequently, in first offset adjustment, zero point correction of the outflow pressure sensor 14 can be performed using atmospheric pressure as a reference. Therefore, in second offset adjustment, zero point correction of the inflow pressure sensor 13 can be performed using the corrected outflow pressure sensor 14 as a reference.

3-3

With the exhalation measurement device, the first offset adjuster 40 may perform first offset adjustment so that the value sensed by the inflow pressure sensor 13 indicates atmospheric pressure, assuming that the exhalation inflow component 9 in a separated state is under an atmospheric pressure environment.

Consequently, when the exhalation inflow component 9 is at atmospheric pressure, zero point correction of the inflow pressure sensor 13 can be performed properly. Also, when the exhalation inflow component 9 is not at atmospheric pressure, the proper zero point correction can be performed by means of second offset adjustment using the measurement result from the exhalation outflow component 10.

3-4

With the exhalation measurement device, the flow regulator 4 may further have the determination component 42, which determines whether or not to perform second offset adjustment with the second offset adjuster 43. The determination component 42 determines not to perform second offset adjustment of the inflow pressure sensor 13 if the output voltage difference is substantially 0 (zero).

Since the exhalation inflow component 9 and the exhalation outflow component 10 are communicating, the actual pressure of the two is the same. Therefore, if the output voltage difference is substantially 0 (zero), that is, if the output voltages of the inflow pressure sensor 13 and the outflow pressure sensor 14 are substantially the same, then it is concluded that the zero point correction of the inflow pressure sensor 13 has been properly performed by the first offset adjustment, and control is performed so that no second offset adjustment will be executed.

3-5

The exhalation measurement device may further comprise the main body case 30 and the open channel 60. The main body case 30 accommodates the flow regulator 4, the chamber 5, the sensor 7, and the pump 8, and has the inlet/outlet holes 30b (an example of second through-holes) that connect the inside and outside. The channel A 601 that links the inlet/outlet holes 30b with the inlet/outlet hole 6a of the open channel 60 constitutes part of the channel, connects the inlet/outlet holes 30b to the inlet/outlet hole 6a, and has a P1 portion and a Q1 portion (examples of first channel wall) that are opposite the inlet/outlet hole 6a and/or the inlet/outlet holes 30b.

The channel B 602 that links the inlet/outlet holes 30b with the inlet/outlet hole 6b of the open channel 60 constitutes part of the channel, connects the inlet/outlet hole 6b and the inlet/outlet holes 30b, and has a P5 portion and a Q5 portion (examples of first channel wall) that are opposite the inlet/outlet hole 6b and/or the inlet/outlet holes 30b.

When wall is thus formed between the inlet/outlet holes 30b and the inlet/outlet holes 6a and 6b so as to be opposite one or the other, or both, when gas flows between the inlet/outlet holes 6a and 6b and the inlet/outlet holes 30b, it will hit the wall portions and changes direction at least once, so fluctuations in gas outside the main body case 30 will be less likely to be directly transmitted into the interior of the chamber 5. Consequently, the turbulence effect that occurs on the exhalation outflow component 10 side can be kept to a minimum, zero point correction of the outflow pressure sensor 14 can be performed more accurately, and second offset adjustment of the inflow pressure sensor 13 on the basis of the value of the outflow pressure sensor 14 can also be performed more accurately.

3-6

With the exhalation measurement device, the open channel 60 may be formed three-dimensionally as shown in FIGS. 6 to 9.

As shown in FIGS. 6 to 9, if we let the direction parallel to the long side of the flat face 50a of the chamber 5 be the X direction, the direction parallel to the short side be the Y direction, and the direction perpendicular to XY be the Z direction, then the first channel 60a and the second channel 60b are formed so that the orientation of the channel changes in the XY direction (two-dimensionally) on the flat face 50a of the chamber 5, and the third channel 60c and the fourth channel 60d are formed in a direction perpendicular to the flat face 50a (the Z direction). Thus varying the orientation of the channel three-dimensionally (in the XYZ direction) means that a gas flowing between the inlet/outlet holes 6a and 6b and the inlet/outlet holes 30b will have to change directions when it hits the channel walls a number of times, so fluctuation of a gas outside the main body case 30 will be less likely to be directly transmitted into the interior of the chamber 5.

3-7

With the exhalation measurement device, the channel A 601 that links the inlet/outlet holes 30b with the inlet/outlet hole 6a of the open channel 60 may constitute part of a channel, and further has the P2 portion, the P3 portion, the P4 portion, the Q2 portion, the Q3 portion, and the Q4 portion (examples of second channel wall) disposed so as to change the flow direction of the gas. An example of these second channel walls is for them to be disposed substantially perpendicular to the P1 portion and the Q1 portion (examples of first channel wall).

Also, the channel B 602 that links the inlet/outlet holes 30b with the inlet/outlet hole 6b of the open channel 60 constitutes part of a channel, and further has the P6 portion, the P7 portion, the P8 portion, the Q6 portion, the Q7 portion, and the Q8 portion (examples of second channel wall) disposed so as to change the flow direction of the gas. An example of these second channel walls is for them to be disposed substantially perpendicular to the P5 portion and the Q5 portion (examples of first channel wall).

Consequently, gas flowing between the inlet/outlet holes 30b and the inlet/outlet holes 6a and 6b has to change its direction upon colliding with the channel walls a number of times, so fluctuation of a gas outside the main body case 30 will be less likely to be directly transmitted into the interior of the chamber 5.

3-8

With the exhalation measurement device, as shown in FIG. 3, the flow regulator 4 may have the wall 17 and the communicating hole 31. The wall 17 is provided between the exhalation inflow component 9 and the exhalation outflow component 10. The communicating hole 31 is formed in the wall 17, and allows the exhalation inflow component 9 to communicate with the exhalation outflow component 10. The adjuster 11 has the valve 32 that is able to open and close the communicating hole 31, and the shaft 33 that is fixed to the valve 32 and is driven by the driver 12. The valve 32 has the elastic member 32a1 that hits the wall 17 around the communicating hole 31 when the communicating hole 31 is closed.

When the valve 32 thus has the elastic member 32a1, it tends to fit snugly against the wall 17, so the communicating hole 31 can be more reliably blocked off by the valve 32.

3-9

With the exhalation measurement device, as shown in FIG. 3, the flow regulator 4 may further have the ring-shaped protrusion 35 that protrudes from the wall 17 so as to surround the communicating hole 31. The elastic member 32a1 hits the protrusion 35 in a state in which the communicating hole 31 has been closed by the valve 32.

Providing this ring-shaped protrusion 35 makes it possible for the communicating hole 31 to be more securely blocked off than when it merely hits the wall 17, without the protrusion 35 being present. This is because manufacturing error or the like can result in a gap when the two faces are in contact.

3-10

The method for controlling the exhalation measurement device may be a method for controlling an exhalation measurement device comprising the handle component 1 into which a user exhales, the flow regulator 4 that is provided downstream from the handle component 1 and adjusts the flow of exhalation blown in from the handle component 1, the chamber 5 that is provided downstream from the flow regulator 4 and temporarily stores exhalation, the inlet/outlet holes 6a and 6b that are provided to the chamber 5 and open up the flow regulator 4 to atmospheric pressure, the sensor 7 that measures a specific component in exhalation, and the pump 8 that is provided downstream from the chamber 5 and sends exhalation into the sensor 7, wherein said method comprises steps S1 to S6 (an example of first offset adjustment steps), steps S7 to S10 (an example of pressure differential detecting steps), and step S12 (an example of a second offset adjustment step), as shown in FIG. 8.

In S1 to S6 (an example of first offset adjustment step), a separated state is created in the flow regulator 4 between the exhalation inflow component 9, where exhalation flows in from the handle component 1 side, and the exhalation outflow component 10, where exhalation flows out to the chamber 5 side, and first offset adjustment is performed on the inflow pressure sensor 13, which senses the pressure of the exhalation inflow component 9, and the outflow pressure sensor 14, which senses the pressure of the exhalation outflow component 10.

In S7 to S10 (an example of pressure differential detecting step), a linked state is created between the exhalation inflow component 9 and the exhalation outflow component 10, and the output voltage difference is detected after the first offset adjustment of the inflow pressure sensor 13 and the outflow pressure sensor 14.

In S12 (an example of a second offset adjustment step), the output voltage difference is used to perform second offset adjustment on the inflow pressure sensor 13.

As discussed above, after first offset adjustment is performed, the difference in output voltage between the inflow pressure sensor 13 and the outflow pressure sensor 14 is used to perform second offset adjustment, so even if there are changes over time, zero point correction of the inflow pressure sensor 13 and the outflow pressure sensor 14 will always be possible under an atmospheric pressure environment during measurement, the effect of changes over time can be suppressed, and the flow established as a guideline can be accurately controlled.

3-11

As shown in FIG. 8, the method for controlling an exhalation measurement device may further comprise a step S11 (an example of a determination step) of determining whether or not to perform second offset adjustment on the basis of the output voltage difference.

In S11 (an example of a determination step), it is determined not to perform the second offset adjustment of the inflow pressure sensor 13 when the output voltage difference is substantially 0 (zero).

Consequently, if there is no need for second offset adjustment, control can be performed so that it is not executed.

(A)

As shown in FIG. 5, the inlet/outlet holes 6a and 6b (an example of first through-holes) may be formed to connect the interior and exterior of the chamber 5, but one-way valves may be further provided to the inlet/outlet holes 6a and 6b.

Figure 12:
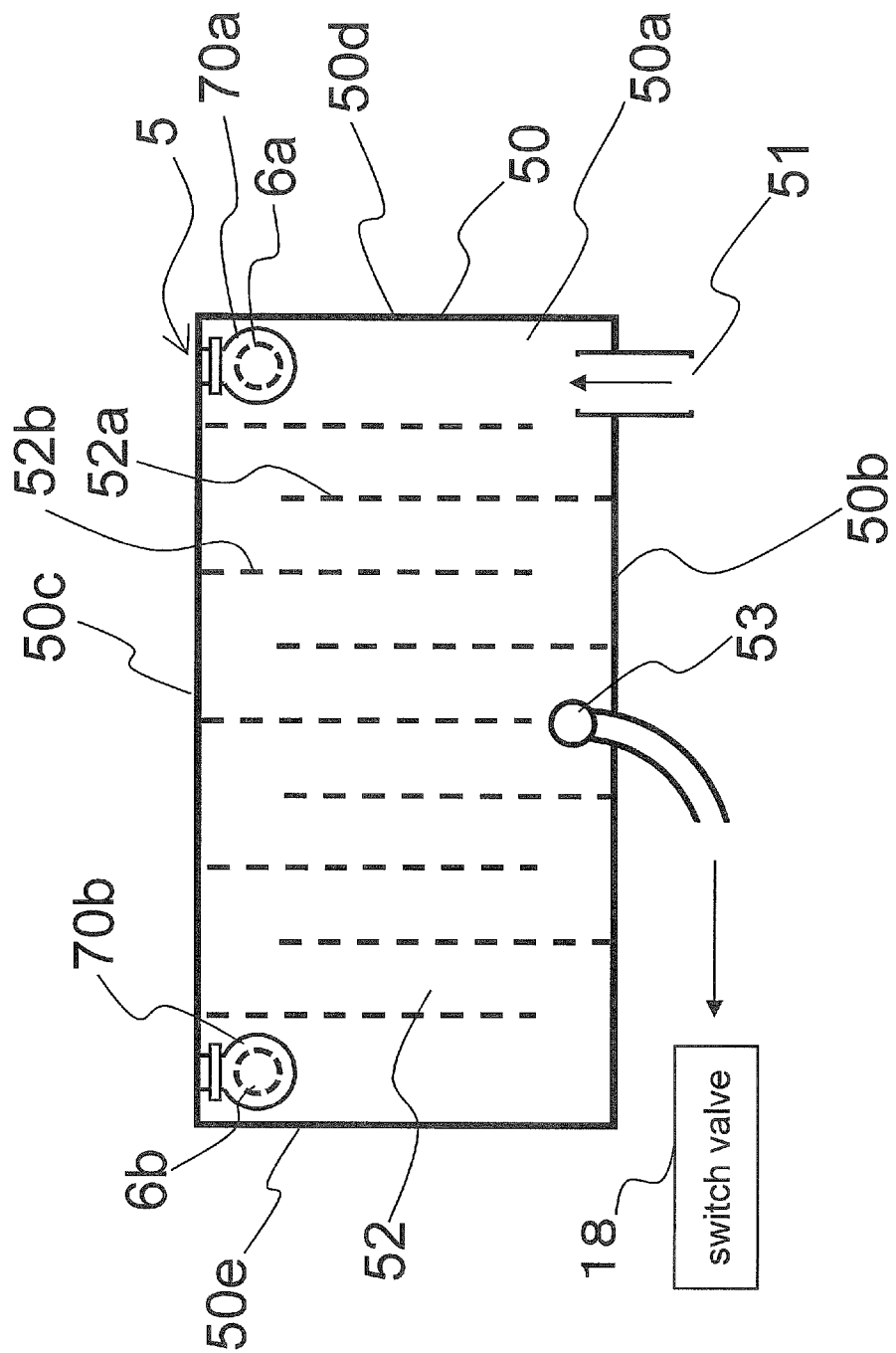
FIG. 12 shows a modification example of a configuration in which the chamber is opened up to the atmosphere.

FIG. 12 shows a state in which one-way valves 70a and 70b are disposed so as to block off the inlet/outlet holes 6a and 6b. The one-way valves 70a and 70b shown in FIG. 12 open up the inlet/outlet holes 6a and 6b when gas is discharged from the chamber 5 to the outside. Meanwhile, the inlet/outlet holes 6a and 6b are kept closed for gas that has flowed in from the outside through the inlet/outlet holes 30b.

(B)

A plurality of walls (P1 to P8 and Q1 to Q8) may be provided near or at the open channel 60 so as to vary the flow direction of gas as shown in FIGS. 6A to 8. There do not need to be a plurality of walls, but it is preferable if a wall that changes the gas flow direction is formed at one or more places.

(C)

Also, the flow regulator controller 15 may be provided separately from the controller 44 that controlled the entire exhalation measurement device, but the flow regulator controller 15 may instead be incorporated into the controller 44.

(D)

Also, in S11, control may be performed so that no further offset adjustment (second offset adjustment) is performed on the inflow pressure sensor 13 if the output voltage (Vs) of the inflow pressure sensor 13 has substantially the same value as the output voltage $V_3$ of the outflow pressure sensor 14, but second offset adjustment may be performed on the inflow pressure sensor 13 even if the values are substantially the same. This is because the formula for the characteristics of the inflow pressure sensor 13 when second offset adjustment is performed is $y=ax+b_2+(V_0-V_2)+(V_3-V_s)$, so if the output voltage (Vs) has substantially the same value as the output voltage $V_3$, then regardless of whether the second offset adjustment is performed or not, the formula for the characteristics of the inflow pressure sensor 13 will be $y=ax+b_2+(V_0-V_2)$, and the result will be the same.

(E)

Also, with the channel A 601 that links the inlet/outlet holes 30b with the inlet/outlet hole 6a of the open channel 60, the P1 and Q1 portions, which are examples of a first channel wall, may be both formed in the top plate 62, but need not be formed in the same plane, and need not be parallel to each other. In this case, the P2, P3, P4, Q2, Q3, and Q4 portions, which are examples of a second channel wall, should be formed substantially perpendicular to either the P1 portion or the Q1 portion (an example of a first channel wall).

The same applies to the channel B 602 that links the inlet/outlet holes 30b with the inlet/outlet hole 6b of the open channel 60. The P5 and Q5 portions, which are examples of a first channel wall, are both formed in the top plate 62, but need not be formed in the same plane, and need not be parallel to each other. In this case, the P6, P7, P8, Q6, Q7, and Q8 portions, which are examples of a second channel wall, should be formed substantially perpendicular to either the P5 portion or the Q5 portion (an example of a first channel wall).

(F)

Also, the open channel 60 may have two channels (the channel A 601 and the channel B 602) that link the interior of the chamber 5 with the exterior of the main body case 30, but may instead have just one channel, or may have three or more channels.

INDUSTRIAL APPLICABILITY

The exhalation measurement device and its control method have the effect of allowing accurate zero point correction to be performed even if turbulence occurs, and are expected to find application in the zero point correction of the flow adjusting pressure sensors of flow regulators provided to exhalation measurement devices that are used in checking pulmonary function, diagnosing asthma, and so forth.

The invention claimed is:

1. An exhalation measurement device, comprising:
    a handle component into which a user exhales;
    a flow regulator that is provided downstream from the handle component and adjusts a flow of exhalation blown in from the handle component;
    a chamber that is provided downstream from the flow regulator and temporarily stores the flow of exhalation;
    an opening component that is provided to the chamber and opens up the flow regulator to atmospheric pressure;
    a measurement component that measures a specific component in the flow of exhalation; and
    a pump that is provided downstream from the chamber and sends the flow of exhalation into the measurement component,
    wherein the flow regulator has:
    an exhalation inflow component where the flow of exhalation flows in from a handle component side;
    an exhalation outflow component where the flow of exhalation flows out to a chamber side;
    a flow adjuster that is provided between the exhalation inflow component and the exhalation outflow component and adjusts the flow of exhalation;
    a driver that drives the flow adjuster;
    an inflow pressure sensor that senses a pressure of the exhalation inflow component and is disposed on an exhalation inflow component side of the flow adjuster;
    an outflow pressure sensor that senses a pressure of the exhalation outflow component and is disposed on an exhalation outflow component side of the flow adjuster; and
    a controller that controls the driver, and
    the controller having:
    a first offset adjuster that causes the driver to drive the flow adjuster and create a separated state between the exhalation inflow component and the exhalation outflow component, and performs first offset adjustment of the inflow pressure sensor and the outflow pressure sensor;
    a voltage difference detector that causes the driver to drive the flow adjuster and create a linked state between the exhalation inflow component and the exhalation outflow component, and detects an output voltage difference after the first offset adjustment of the inflow pressure sensor and the outflow pressure sensor; and
    a second offset adjuster that uses the output voltage difference to perform second offset adjustment of the inflow pressure sensor.

2. The exhalation measurement device according to claim 1,
    wherein the exhalation outflow component in the separated state is under an atmospheric pressure environment, and
    the first offset adjuster performs the first offset adjustment so that a sensed value of the outflow pressure sensor indicates atmospheric pressure.

3. The exhalation measurement device according to claim 1,
    wherein the exhalation inflow component in the separated state is assumed to be under an atmospheric pressure environment, and the first offset adjuster performs the first offset adjustment so that a sensed value of the inflow pressure sensor indicates atmospheric pressure.

4. The exhalation measurement device according to claim 1,
    wherein the flow regulator further has a determination component that determines whether or not to perform the second offset adjustment with the second offset adjuster, and
    the determination component determines not to perform the second offset adjustment of the inflow pressure sensor when the output voltage difference is substantially 0 (zero).

5. The exhalation measurement device according to claim 1,
    wherein the opening component has a first through-hole that connects an inside of the chamber with an outside of the chamber.

6. The exhalation measurement device according to claim 5,
    wherein the opening component further has a one-way valve disposed so as to cover the first through-hole, and
    the one-way valve allows gas to pass from the inside of the chamber toward the outside of the chamber.

7. The exhalation measurement device according to claim 5, further comprising:
    a main body case that houses the flow regulator, the chamber, the measurement component, and the pump, and that has a second through-hole that connects the inside of the chamber and the outside of the chamber; and
    an open channel that connects the first through-hole and the second through-hole,
    wherein the open channel has a first channel wall that constitutes part of the open channel and is opposite the first through-hole and/or the second through-hole.

8. The exhalation measurement device according to claim 7,
    wherein the open channel is formed three-dimensionally.

9. The exhalation measurement device according to claim 7,
    wherein the open channel further has a second channel wall that constitutes part of the open channel and is disposed substantially perpendicularly to a direction of gas flow, and the second channel wall is disposed substantially perpendicularly to the first channel wall.

10. The exhalation measurement device according to claim 1,
    wherein the flow regulator has:
    a wall that is provided between the exhalation inflow component and the exhalation outflow component; and
    a communicating hole that is formed in the wall and allows the exhalation inflow component to communicate with the exhalation outflow component;
    and wherein the flow adjuster has:
    a valve that can open and close the communicating hole; and
    a shaft that is fixed to the valve and is driven by the driver, and
    the valve has an elastic member that hits an area of the wall around the communicating hole in a state in which the communicating hole is closed.

11. The exhalation measurement device according to claim 10,
    wherein the flow regulator further has a ring-shaped protrusion that sticks out from the wall so as to surround the communicating hole, and
    the elastic member hits the ring-shaped protrusion in a state in which the communicating hole has been closed by the valve.

12. A method for controlling an exhalation measurement device comprising:

a handle component into which a user exhales;

a flow regulator that is provided downstream from the handle component and adjusts a flow of exhalation blown in from the handle component;

a chamber that is provided downstream from the flow regulator and temporarily stores the flow of exhalation;

an opening component that is provided to the chamber and opens up the flow regulator to atmospheric pressure;

a measurement component that measures a specific component in the flow of exhalation; and a pump that is provided downstream from the chamber and sends the flow of exhalation into the measurement component, wherein the flow regulator has:

an exhalation inflow component where the flow of exhalation flows in from a handle component side;

an exhalation outflow component where the flow of exhalation flows out to a chamber side;

a flow adjuster that is provided between the exhalation inflow component and the exhalation outflow component and adjusts the flow of exhalation;

a driver that drives the flow adjuster;

an inflow pressure sensor that senses a pressure of the exhalation inflow component and is disposed on an exhalation inflow component side of the flow adjuster;

an outflow pressure sensor that senses a pressure of the exhalation outflow component and is disposed on an exhalation outflow component side of the flow adjuster; and a controller that controls the driver, wherein said method comprises:

a first offset adjustment step of causing the driver to drive the flow adjuster and create a separated state between the exhalation inflow component and the exhalation outflow component, and performing a first offset adjustment of the inflow pressure sensor and the outflow pressure sensor;

a voltage difference detecting step of causing the driver to drive the flow adjuster and create a linked state between the exhalation inflow component and the exhalation outflow component, and detecting an output voltage difference after the first offset adjustment of the inflow pressure sensor and the outflow pressure sensor; and a second offset adjustment step of using the output voltage difference to perform a second offset adjustment of the inflow pressure sensor.

13. The method for controlling an exhalation measurement device according to claim 12, further comprising a determination step of determining whether or not to perform the second offset adjustment on the basis of the output voltage difference, wherein the determination step involves determining not to perform the second offset adjustment of the inflow pressure sensor when the output voltage difference is substantially 0 (zero).

* * * * *